(12) United States Patent
Wensbo Posaric et al.

(10) Patent No.: US 9,499,572 B2
(45) Date of Patent: Nov. 22, 2016

(54) PHOSPHATIDYLALKANOLS AND COMPOSITIONS THEREOF

(71) Applicant: Pethmark AB, Södertälje (SE)

(72) Inventors: David Wensbo Posaric, Malmö (SE); Karl-Erik Berquist, Lund (SE)

(73) Assignee: Pethmark AB, Sodertalje (SE)

( * ) Notice: Subject to any disclaimer, the term of this patent is extended or adjusted under 35 U.S.C. 154(b) by 0 days.

(21) Appl. No.: 14/888,802

(22) PCT Filed: Apr. 30, 2014

(86) PCT No.: PCT/SE2014/050543
§ 371 (c)(1),
(2) Date: Nov. 3, 2015

(87) PCT Pub. No.: WO2014/178787
PCT Pub. Date: Nov. 6, 2014

(65) Prior Publication Data
US 2016/0052946 A1    Feb. 25, 2016

(30) Foreign Application Priority Data

May 3, 2013   (SE) ...................... 1330045
Jan. 23, 2014  (SE) ...................... 1430005

(51) Int. Cl.
| C07F 9/11 | (2006.01) |
| C07F 9/10 | (2006.01) |
| G01N 24/08 | (2006.01) |

(52) U.S. Cl.
CPC ............... C07F 9/106 (2013.01); C07F 9/11 (2013.01); G01N 24/08 (2013.01)

(58) Field of Classification Search
CPC .................... C07F 9/106; C07F 9/11
See application file for complete search history.

(56) References Cited

U.S. PATENT DOCUMENTS 5,279,833 A * 1/1994 Rose ...................... C12N 15/88 424/450
6,372,714 B1 * 4/2002 Tanaka ................. A61K 9/1272 264/4.1

FOREIGN PATENT DOCUMENTS

| JP | 11174139 A | 7/1999 |
| WO | 2012005680 A | 1/2012 |

OTHER PUBLICATIONS

International Search Report for PCT/SE2014/050543 dated Aug. 8, 2014.
Written Opinion of the International Searching Authority dated Aug. 8, 2014.
Mahajan, Shivani, et al., Determining and reporting purity of organic molecules: why qNMR, Wiley Online Library, Dec. 12, 2012.
Rundlof, Torgny, Survey and qualification of internal standards for quantification by H NMR spectroscopy. Journal of Pharmaceutical and Biomedical Analysis, 52 (2010) 645-651, Feb. 11, 2010.
Sigma, Product Information for 1,2 Diacyl-sn-glycero-3-phosphocholine, Sigma-aldrich.com, May 2003.
STN International, file registry, RN 1185244-35-2, Entered STN, Sep. 17, 2009.
Vyssotski, Mikhail, et. al, TLC and 31P-NMR Analysis of Low Polarity Phospholipids, Lipids 44:381-389, Dec. 13, 2008.
Gnann, H., et al., Identification of 48 homologues of phosphatidylethanol in blood by LC-ESI-MS/MS, Anal Bioanal Chem (2010) 396:2415-2423, Feb. 2, 2010.
Kihara, Masaru, et. al., Isolation and Structure Elicidation of a Novel Alkaloid, Incartine, a Supposed Biosynthetic Intermediate, from Flowers of Lycoris incarnata, Chem. Pharm. Bull. 42(2) 289-292, Feb. 1994.
Lancee-Hermkens, A.M.W., et al., C NMR Measurements of Unsonicated Phosphatidylcholine Bilayers of Different Fatty Acid and Sterol Composition, Biochimica et Biophysica Acta, 470 (1977) 141-151, Mar. 23, 1977.
Lehnhardt, Fritz-Georg, et al., H- and P-MR spectroscopy of primary and recurrent human brain tumors in vitro: malignancy-characteristic profiles of water soluble and lipophilic spectral components, NMR In Biomedicine, 2001; 14:307-317.
Nalesso, Alessandro, Quantitative Profiling of phosphatidylethanol molecular species in human blood by liquid chromatography high resolution mass spectrometry, Journal of Chromatography A, 1218 (2011) 8423-8431, Oct. 1, 2011.
Wensbo Posaric, David, et. al., Differentiation and quantification of synthetic phosphatidylethanol (PEth) homologues by H- and C-NMR in polar organic solvents, Anal Bioanal Chem (2014) 406: 4735-4744, May 28, 2014.
Willmann, Jan, Combined Reversed Phase HPLC, Mass Spectrometry, and NMR Spectroscopy for a Fast Separation and Efficient Identification of Phosphatidylcholines, Journal of Biomedicine and Biotechnology, vol. 2011, Article ID 385786, 8 pages, Jul. 21, 2010.
Zheng, Yufang, et al., Method development for routine liquid chromatography-mass spectrometry measurement of the alcohol biomarker phosphatidylethanol (PEth) in blood, Clinica Chimica Acta 412 (2011) 1428-1435, Apr. 19, 2011.
Translation of Swedish Office Action in Swedish patent application No. 1330045-4, dated Mar. 3, 2010.

* cited by examiner

Primary Examiner — Golam M M Shameem
(74) Attorney, Agent, or Firm — Kim Winston LLP

(57) ABSTRACT

The present invention discloses a composition comprising a compound of formula I and a deuterated solvent. The deuterated solvent is miscible with water in any proportion at a temperature of 20 to 25° C. and comprises less than 5% residual $^1$H-isotopes. The concentration of the compound of formula I may advantageously be determined by $^1$H-QNMR. Methods of production of the composition and salts of compounds of formula I, as well as related analogs and novel reagents and intermediates for the production thereof, are also described.

4 Claims, 11 Drawing Sheets

PHOSPHATIDYLALKANOLS AND COMPOSITIONS THEREOF

CROSS-REFERENCE TO RELATED APPLICATIONS

This application is a U.S. national phase application under 35 U.S.C. §371 of International Application No. PCT/SE2014/050543 filed on Apr. 30, 2014 which claims priority to Swedish Patent Application No. 1430005-7 filed Jan. 23, 2014 and Swedish Patent Application No. 1330045-4 filed on May 3, 2013, the entire disclosures of which are hereby incorporated by reference in their entirety.

TECHNICAL FIELD

The present invention relates to compositions, in particular water miscible compositions, comprising phosphatidylalkanols, in particular phosphatidylethanol-homologues (PEth-homologues), in which the concentration of the phosphatidylalkanol constituent can be determined by quantitative nuclear magnetic resonance spectroscopy (QNMR).

BACKGROUND

Prolonged and high consumption of alcohol (ethanol) may lead to serious alcohol-related diseases and alcoholism in man. On the other hand, a low to moderate consumption is commonly accepted as being associated with a reduced risk of coronary heart disease, possibly due to an antiatherogenic effect of ethanol. In order to be able to classify a person's drinking behavior, or to more accurately direct medical investigations in the search for an underlying cause of one or several observed symptoms, slow eliminating bio-markers of ethanol are highly useful as objective measures of the person's historic alcohol consumption. Phosphatidylethanol (PEth), an unnatural phospholipid formed by phospholipase D catalyzed ethanolysis in-vivo of mainly endogenous phosphatidylcholine, has recently gained high interest as such a slow eliminating bio-marker. Today, LC-MS-based analytical techniques are commonly used for the quantification of PEth in human blood-samples. One or a few PEth-homologues, such as PEth-16:0/18:1 and/or PEth-16:0/18:2, are usually quantified and used as a representative measure of the total PEth-level.

Nalesso et al. (Journal of Chromatography, 2011, 8423-8431) describe the development of a novel LC-HRMS based method for the quantitative profiling of PEth molecular species in human blood from heavy and social drinkers. Commercially available chloroform solutions of the sodium salt of 1,2-dipalmitoyl-sn-glycero-3-phosphoethanol (PEth-16:0/16:0), 1,2-dioleoyl-sn-glycero-3-phosphoethanol (PEth-18:1/18:1) and 1,2-dioleoyl-sn-glycero-3-phosphobutanol (PBut-18:1/18:1) were used as reference materials and internal standard, respectively, for the qualitative and/or quantitative determination of various PEth-homologues.

Zheng et al. (Clinica Chimica Acta, 2011, 1428-1435) describe an LC-ESI-MS(/MS) method for the simultaneous qualitative and quantitative determination of PEth forms in whole blood samples. Commercially available or synthetically produced PEth-16:0/18:1, PEth-16:0/18:2, deuterium labeled PEth-16:0/18:1, deuterium labeled PEth-16:0/18:2 and phosphatidylpropanol (PProp-18:1/18:1) were used as reference materials or internal standards for the qualitative and/or quantitative determination of various PEth-homologues.

WO2012005680 A1 discloses methods for assessment of previous ethanol exposure by obtaining a ratio between one or several bio-precursors of PEth and one or several PEth-homologues in a sample. Methods comprising the step of removal of the carboxylic acid residues of PEth by selective hydrolysis or selective transesterification followed by quantification of the resulting respective products are also disclosed.

Quantitative nuclear magnetic resonance (QNMR) spectroscopy is widely accepted as a qualitative and quantitative analytical tool. QNMR may be used as an alternative or complementary technique to traditional analytical methods, such as e.g. methods relying on chromatographic separation of organic compounds, for the quantification of one or several compounds of interest. A major advantage of QNMR, in comparison to most traditional analytical methods, is the lack of requirement of an identical standard reference material for quantitative determination of an organic compound of interest in solution. Useful nuclei for quantitative determination employing QNMR-techniques include $^1$H ($^1$H-QNMR), $^{31}$P ($^{31}$P-QNMR) and $^{19}$F ($^{19}$F-QNMR), of which the former is generally the most useful due a wide occurrence in combination with generally sharp signals, from which desired accurate and precise raw data may be collected.

JPH11174139 A1 discloses a method for quantitative determination of a mixture comprising a surface active agent utilizing $^1$H-QNMR by employment of an internal standard.

Nuclear magnetic resonance (NMR) analysis of the $^1$H- ($^1$H-NMR) and $^{13}$C- ($^{13}$C-NMR) nuclei of lipophilic lipids, including PEth, its less lipophilic major bio-precursor phosphatidylcholine (PC) and the structurally related phosphatidylethanolamine (PE), is most commonly conducted in fat solubilizing lipophilic solvents, typically deuterated chloroform ($CDCl_3$), with an optional additive of deuterated methanol ($CD_3OD$) as a minor component in the case of e.g. PC.

Kihara et al. (Chem. Pharm. Bull., 1994, 289-292) used $CDCl_3$ as solvent for the $^1$H-NMR analysis of PE-16:0/18:2 (compound 12) and the sodium salt of 1-palmitoyl-2-linoleoylphosphatidylmethanol (compound 13), the latter of which is highly structurally and physiochemically similar to PEth-16:0/18:2.

Willmann et al. (Journal of Biomedicine and Biotechnology, 2011, 1-8) used a 2:1-mixture of $CDCl_3$ and deuterated methanol ($CD_3OD$) for the $^1$H- and $^{13}$C-NMR analysis of various phosphatidylcholines (PCs).

Lehnhardt et al. (NMR Biomed. 2001, 307-317) used deuterated water ($D_2O$) as solvent and 3-(trimethylsilyl) propionic acid as internal standard in the quantitative determination by $^1$H-QNMR of various phospholipids, although not including PEth or any other alkyl-analog thereof. Quantitative determination of such lipids employing $^{31}$P-QNMR in a matrix comprising a 8:2-mixture of water and $D_2O$, Na-cholate and EDTA, using phosphono-methyl-glycerol as internal reference, is also described therein.

Vyssotski et al. (Lipids, 2009, 381-389) describes quantitative determination of various lipids, including PEth and alkyl analogs, employing $^{31}$P-QNMR in a matrix comprising a 8:2-mixture of water and $D_2O$, Na-cholate and EDTA, using phosphonomethylglycine as internal reference.

Lancée-Hermkens et al. (Biochimica et Biophysica Acta, 1977, 141-151) describes $^{13}$C-NMR analysis of PC bilayers of different fatty acid and sterol composition. NMR-spectra were run in a $D_2O$-based matrix. It was observed that cholesterol interacted with PC, which interaction generally manifested itself in an increased line broadening of the $^{13}$C-NMR signals of the hydrophobic part of the PC. This result suggests that $^1$H-NMR signals of similar lipids, e.g. PEth, may broaden in the presence of other amphiphilic components, such as e.g. Na-cholate or the like, in a polar solvent.

Currently, all LC-MS-based methods employed for quantitative determination of phosphatidylalkanols, such as e.g. PEth, in blood samples, including those mentioned herein above, rely on analytical reference solutions, typically solutions comprising a single phosphatidylalkanol or analog in which the concentration thereof is known, for development of standard curves for quantification and/or quantitative instrument calibration. The standard laboratory technique, used for the preparation of such reference solutions involve precise weighing of the reference compound, followed by addition to a precise volume of a suitable solvent. The error in the final concentration of the reference is dependent of factors including e.g. weighing-errors, errors in the assumption of the purity of the reference material, error in the measurement of the volume of solvent and errors related to incomplete dissolution of the reference material. Furthermore and importantly, the error in the final concentration of the reference translates to an error in the determined concentration of the phosphatidylalkanol, such as e.g. PEth, in the analyzed sample.

Hence, improved compositions comprising phosphatidylalkanols, such as e.g. an improved reference solution of a phosphatidylalkanol, are desired for a simplified, more precise and/or more accurate determination of phosphatidylalkanols, such as e.g. PEth, in samples, such as e.g. human blood samples. In addition, improved regio- and stereoselective methods of production of such novel and/or presently known PEth-homologues and/or derivatives are also needed.

SUMMARY

It is an object of the present invention, considering the disadvantages mentioned above, to provide a composition comprising a phospahtidylalkanol in which the concentration thereof can be determined by a technique that does not rely on the precise weighing of that phosphatidylalkanol in the production of the composition.

It is another object of the present invention to provide a composition comprising a phospahtidylalkanol, in which the concentration thereof can be determined by a technique that does not rely on the knowledge of the precise purity of that phosphatidylalkanol prior to the production of the composition.

It is another object of the present invention to provide a composition comprising a phospahtidylalkanol, which composition is miscible with water or aqueous solutions to allow for the preparation by dilution of aqueous analytical reference solutions with a known concentration of the phosphatidylalkanol without the need of removal of a solvent not being miscible with water.

It is another object of the invention to provide compounds which may be used as analytical reference materials for enabling improved determination of a person's historic ethanol consumption.

These and other objects, which will appear from the following description, have now been achieved by a composition, according to one aspect of the present invention, which comprises a compound of formula I

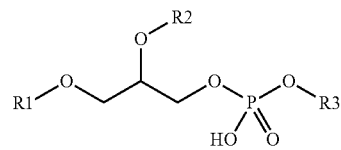

or any salt, diastereomer, enantiomer, racemic mixture, scalemic mixture or isotopically enriched form thereof and a deuterated solvent, preferably a deuterated aprotic polar solvent, for determination of the concentration of the compound of formula I by $^1$H-QNMR, wherein R1 is selected from the group consisting of —C(=O)—C2-25 straight alkyl, —C(=O)—C2-25:1-6 straight alkenyl and —C(=O)-A-Q; R2 is selected from the group consisting of —C(=O)—C2-25 straight alkyl, —C(=O)—C2-25:1-6 straight alkenyl and —C(=O)-A-Q; R3 is —C1-6 alkyl; A is a linker group comprising 2 to 20 carbon atoms; Q is a spectrophotometrically or fluorometrically detectable moiety comprising at least one aromatic carbocycle or heterocycle; the sum of the compound of formula I and any salt form, diastereomer, enantiomer, racemic mixture, scalemic mixture and isotopically enriched form thereof exceeds 0.05 μmol/g of the composition; and the deuterated solvent is miscible with water in any proportion at a temperature of 20 to 25° C. and comprises less than 5% residual $^1$H-isotopes.

The concentration of the compound of formula I of the present composition may advantageously be determined by QNMR, including $^1$H-QNMR and $^{31}$P-QNMR. Furthermore, such QNMR techniques allow for non-destructive periodic monitoring of the concentration, without even having to open the container in which the composition is stored provided that this container is a suitable NMR-tube. Hence, the analytical chemist may readily check his or hers analytical reference solutions when being in the form of the present composition.

According to another aspect of the present invention, the compound of formula I may be isotopically enriched with deuterium, or any other suitable heavy isotope as known in the art.

The molecular weight of such an isotopically enriched compound of formula I is higher than the corresponding compound which is not isotopically enriched, whereby analytical differentiation by employment of e.g. LC-MS(/MS) is permitted. Hence, such an isotopically enriched compound of formula I may, for example, advantageously be used as analytical reference by spiking samples, in which the not isotopically enriched compound of formula I is being quantified, with a known amount.

According to yet another aspect of the present invention, the deuterated solvent may have a boiling point exceeding 100° C. at atmospheric pressure.

Such a relatively high boiling point results advantageously in a relatively low spontaneous evaporation of the deuterated solvent from the composition when stored in an open container at ambient temperature. The change in concentration of the compound of formula I in the composition is thus minimized upon, for example, repeated opening and closing of the storage container when removing aliquots for use in e.g. the quantitative calibration of analytical instruments.

According to yet another aspect of the present invention, the composition may further comprise an amphiphilic additive in an amount exceeding 1 mg/g of the composition. The amphiphilic additive may be a detergent selected from the group consisting of anionic-, cationic-, non-ionic- and zwitterionic detergents.

Advantages of the presence of an amphiphilic additive in the present composition include the increase in solubility of the compound of formula I. Hence, the composition may comprise a relatively high concentration of the compound of formula I, whereby the determination of the concentration by e.g. QNMR is facilitated and can be done with a higher precision. Furthermore, the risk of precipitation of the compound of formula I upon the addition of the composition to an aqueous matrix is minimized due to the chemical interaction of the amphiphilic additive.

According to yet another aspect of the present invention, the composition may further comprise an internal reference, wherein the internal reference: is present in an amount to allow detection by NMR in period of time which is essentially equal to or less than the period of time needed for detection by NMR of the compound of formula I; and bring forth at least one NMR signal pertaining to an investigated nucleus, which NMR-signal is suitable for integration and which is essentially separated from all NMR-signals of the compound of formula I pertaining to the same investigated nucleus, upon the generation of an NMR-spectrum of the composition.

Advantages of an internal reference include the readily commercial availability of suitable internal references which are validated for use in QNMR. Hence, no separate validation of another component of the composition which bring forth at least one suitable reference NMR-signal, is needed.

According to yet another aspect of the invention, the composition may further comprise an additive selected from the group consisting of a strong solvents, polar modifiers, antioxidants, preservatives, pH adjusting agents, colorants and drying agents.

Such an additive, in particular strong solvents and polar modifiers, may advantageously slightly change the shift or improve the line shape or resolution of the NMR-signals of compounds of formula I, so that integrals thereof may be collected with a higher precision in QNMR applications. Such an additive, in particular antioxidants, preservatives, pH adjusting agents, colorants and drying agents, may further increase the stability of the compound of formula I, whereby the decrease in concentration over time is minimized.

According to yet another aspect of the present invention, there is provided a salt of a compound of formula I

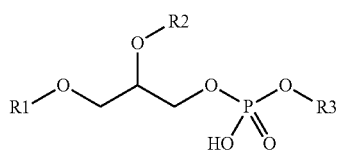

(I)

or any diastereomer, enantiomer, racemic mixture, scalemic mixture or isotopically enriched form thereof, wherein R1 is selected from the group consisting of —C(=O)—C2-25 straight alkyl, —C(=O)—C2-25:1-6 straight alkenyl and —C(=O)-A-Q; R2 is selected from the group consisting of —C(=O)—C2-25 straight alkyl, —C(O)—C2-25:1-6 straight alkenyl and —C(=O)-A-Q; R3 is ethyl; A is a linker group comprising 2 to 20 carbon atoms; Q is a spectrophotometrically or fluorometrically detectable moiety comprising at least one aromatic carbocycle or heterocycle; and the salt is selected from the group consisting of ammonium salts, alkylammonium salts, dialkylammonium salts in which the alkyl groups are independently selected alkyl groups and trialkylammonium salts in which the alkyl groups are independently selected alkyl groups.

Such salts have, in contrast to the parent protonated form of compounds of formula I, which tend to exist in the form of thick sticky syrups, a greater tendency to exist in a solid amorphous or crystalline form which is easier to handle in the preparation of e.g. the present composition.

According to yet another aspect of the present invention, there is provided a compound according to Formula II or any diastereomer, enantiomer, racemic mixture, scalemic mixture or isotopically enriched form thereof,

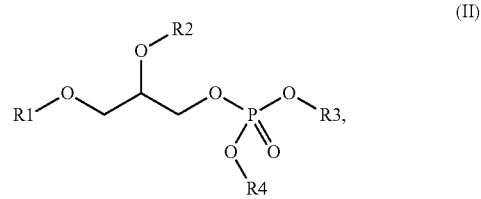

(II)

wherein R1 is C(=O)—C13-25 straight alkyl or C(=O)—C13-25 straight alkenyl, C(=O)—C13-25 straight alkenyl is comprising at least one carbon-carbon double-bond; R2 is selected from the group consisting of H, C(=O)—C13-25 straight alkyl and C(=O)—C13-25 straight alkenyl, C(=O)—C13-25 straight alkenyl is comprising at least one carbon-carbon double-bond; R1 is C(=O)—C13-25 straight alkyl when R2 is C(=O)—C13-25 straight alkenyl; R2 is H or C(=O)—C13-25 straight alkyl when R1 is C(=O)—C13-25 straight alkenyl; R3 is ethyl or CD2CD3; R4 is H, HN(R5)3 or CH2CH2CN; R5 is independently selected from H and C1-6 alkyl; and R1 is C(=O)—C13-25 straight alkenyl when R4 is H.

Advantages of such compounds include, for example, the improved usability as analytical reference materials as compared to related compounds of the prior art.

According to yet another aspect, there is provided a method for production of a compound of the invention, comprising the step of use of a compound of Formula III or racemate thereof, wherein R3 is e.g. ethyl or CD2CD3, as a chemical intermediate

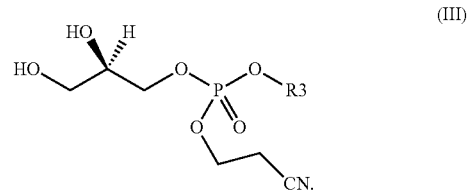

(III)

Advantages of use of such a compound as chemical intermediate include, for example, the improved yield in the production of compounds of Formula I or II as compared to methods of the prior-art aiming at the same type of products.

According to yet another aspect, 2-cyanoethoxy-(1,1,2,2,2-petadeuteroethoxy)-(N,N-diisopropylamino)phosphine may be used a chemical reagent in the synthesis of compounds of Formula I, II or III. Advantages of use of such a compound as chemical reagent include, for example, the improved yield in the production as compared to methods of the prior-art aiming at the same type of products. Furthermore, such a reagent enables the use a large variety of starting materials for introduction of the 1,1,2,2,2-petadeuteroethoxy-group, in comparison to methods of the prior-art restricted to the use of phosphatidylcholines as starting material.

According to yet another aspect of the present invention, there is provided a method of production of the composition, comprising the steps of: (i) treating the compound of formula I with the deuterated solvent, preferably a deuterated aprotic polar solvent, until all or a part of the compound of formula I is dissolved in the deuterated solvent, to obtain a first intermediate composition; and (ii) if the first intermediate composition comprise any heterogeneous matter, optionally remove the heterogenous matter by filtration or decantation.

This method of preparation results advantageously in a composition which has a low chance of being supersaturated with regard to the compound of formula I. The risk of subsequent precipitation of a part of the compound of formula I, whereby the concentration of the compound of formula I in the composition is decreased, is thus minimized.

According to yet another aspect of the present invention, there is provided a method of production of the composition, comprising the steps of: (i) treating the compound of formula I with a strong solvent until all or a part of the compound of formula I is dissolved in the strong solvent, to obtain a second intermediate composition; (ii) mixing the second intermediate composition with the deuterated solvent, preferably a deuterated aprotic polar solvent, to obtain a third intermediate composition; (iii) removing more than 95% of the strong solvent from the third intermediate composition by distillation or evaporation, to obtain a fourth intermediate composition; and (iv) if the fourth intermediate composition comprise any heterogeneous matter, optionally remove the heterogenous matter by filtration or decantation, wherein the strong solvent has a boiling point of at least 20° C. less than the boiling point of said deuterated solvent and in which the solubility of the compound of formula I is at least 1 mg/ml of the strong solvent a temperature of 25° C.

This method of production is advantageously relative fast in comparison to other methods which are dependant on the kinetics of dissolution of the compound of formula I in the deuterated solvent. Furthermore, trace amounts of residing residual strong solvent in the final composition results in a downfield shift of $^1$H-NMR signals from protons most adjacent the phosphorous atom of compounds of formula I. This downfield shift may advantageously result in a more facile integration of these signals in $^1$H-QNMR-applications as compared to the case with no trace amounts of the strong solvent present.

According to yet another aspect of the present invention, there is provided a method for determination of the concentration of a compound of formula I in the composition by QNMR, comprising the steps of: (i) collecting at least two NMR signals pertaining to an investigated nucleus of the composition; (ii) collecting the integral of at least one isolated NMR signal brought forth by the compound of formula I and at least one isolated NMR signal brought forth by a determinative component; and (iii) calculating the concentration of the compound of formula I on the basis of the integrals collected in step (ii), wherein the amount of the determinative component or the concentration of the determinative component in the composition is known; the determinative component is selected from the group consisting of residual protonated solvent in the deuterated solvent, preferably a deuterated aprotic polar solvent, when the investigated nucleus of the composition is $^1$H, the amphiphilic additive, the internal reference, an external reference and the additive.

Determination of the concentration by employment of QNMR techniques allow for non-destructive periodic monitoring of the concentration, without even having to open the container in which the composition is stored provided that this container is a suitable NMR-tube. Hence, the analytical chemist may readily check his or hers analytical reference solutions when being in the form of the present composition.

Further features of the invention and its embodiments are set forth in the appended claims.

BRIEF DESCRIPTION OF THE FIGURES

Regions of particular interest of $^1$H-NMR spectra run at a 400 MHz spectrometer of PEth-16:0/18:1, a compound of formula I, in its parent protonated form, in its trimethylamine salt form, or in its ammonium salt form, in various solvents and with or without amphiphilic additives and/or internal references, are depicted in FIGS. 1 to 11 below. The signals originating from various hydrogen atoms of PEth-16:0/18:1 are marked in the FIGS. 1 to 11 as indicated in the drawing below, and those originating from an amphiphilic additive or internal reference as $H_{add}$ and $H_{ref}$ respectively. The signals marked with $H_{add}$ represent signals of the amphiphilic additive that may be used as $^1$H-QNMR reference signals for quantification of the compound of formula I, in particular when separated from all signals of the compound of formula I, according to various embodiments of the invention. The signals marked in the FIGS. 1 to 11 as indicated in the drawing below represent signals that may be used as $^1$H-QNMR representative signals of compounds of formula I for quantification of the compound of formula I, in particular when separated from all other signals of the composition, according to various embodiments of the invention. Unless otherwise noted, the internal reference for which the corresponding signal ($H_{ref}$) is indicated in FIGS. 1 to 11, is dimethyl sulfone (CAS-no: 67-71-0).

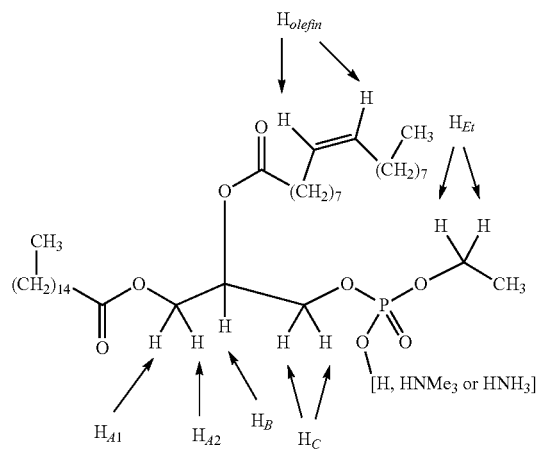

Indicated groups of protons of the protonated form, the trimethyl amine salt form and the ammonium salt form of PEth-16:0/18:1.

Figure 1:
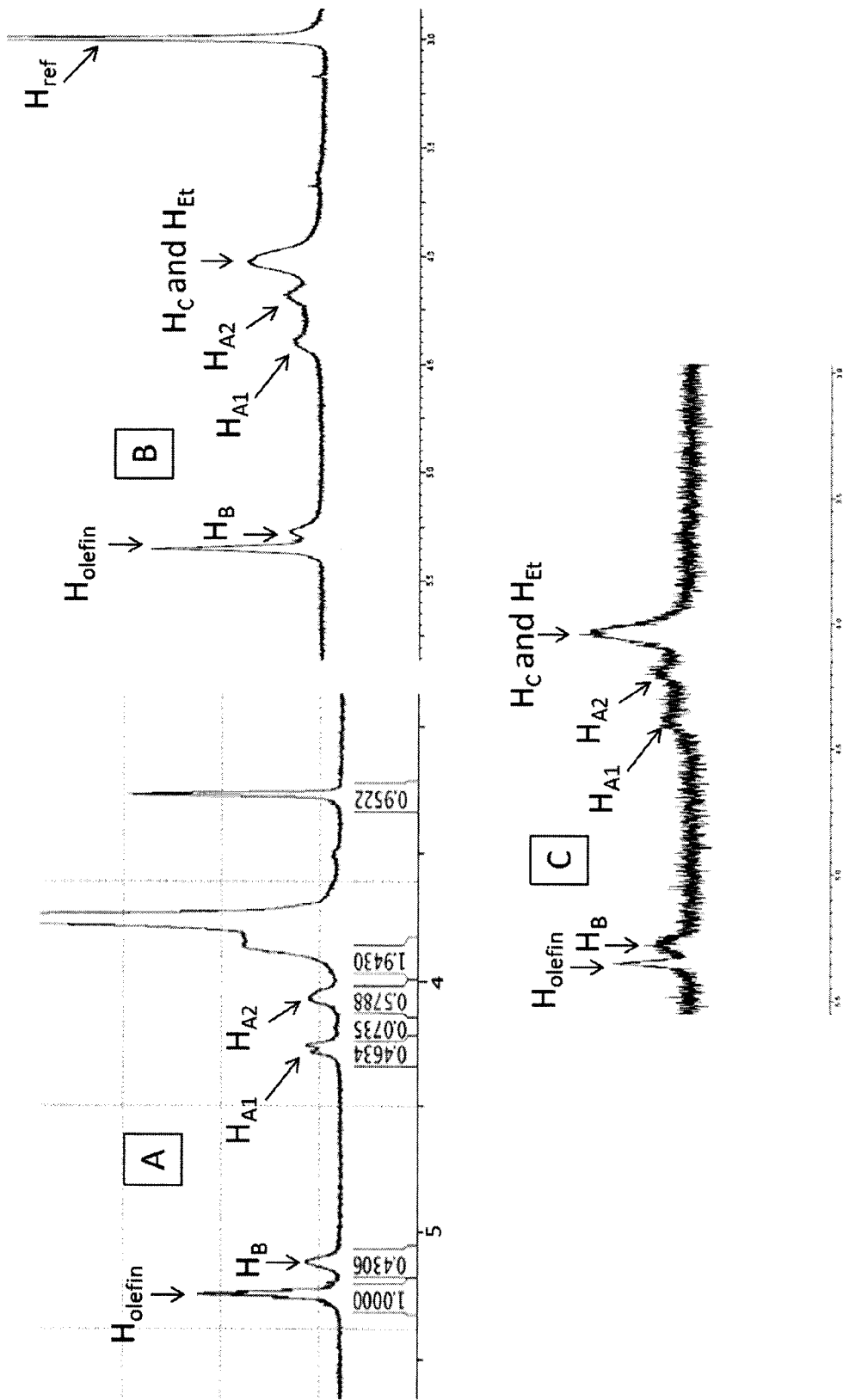
Figure 2:
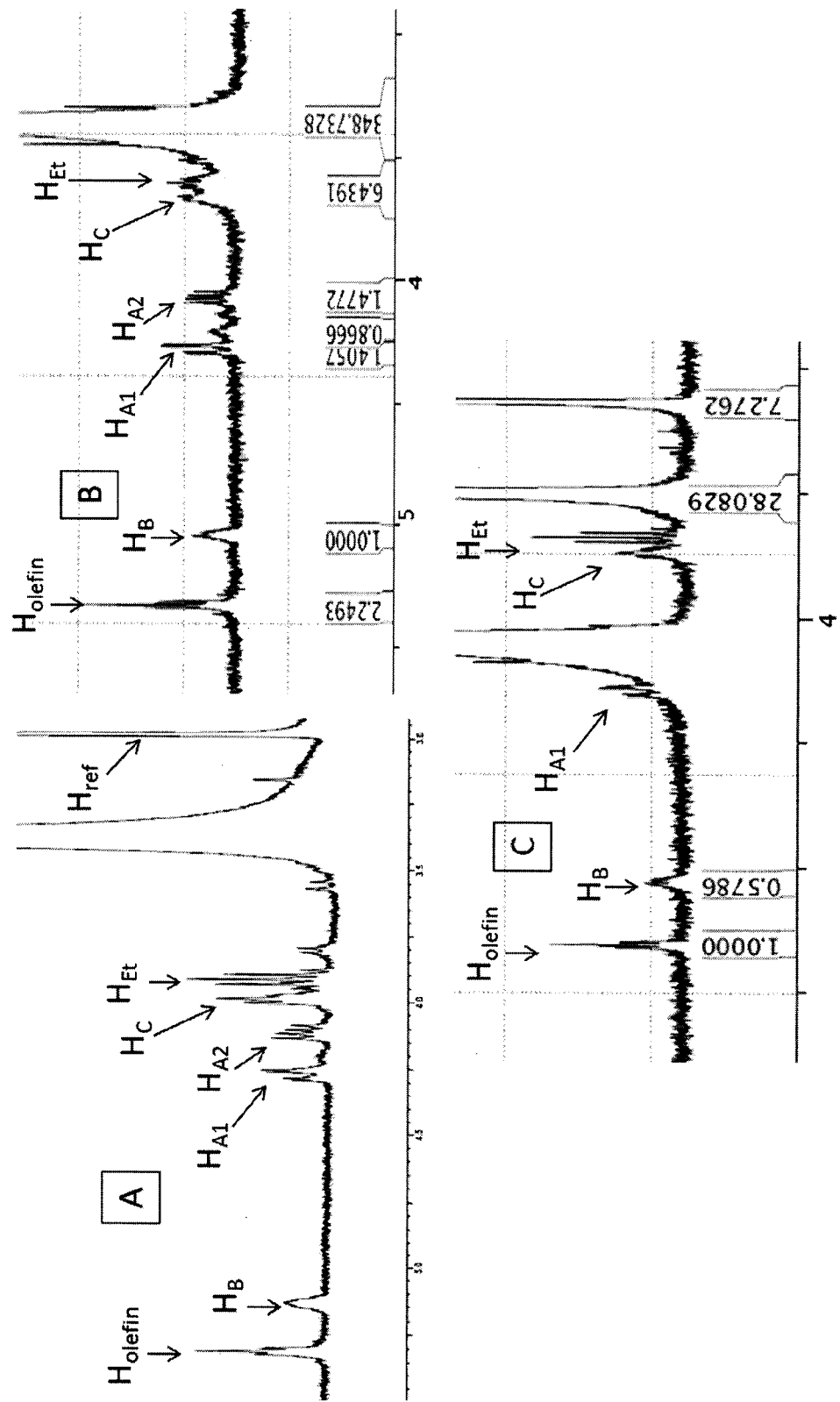
Figure 3:
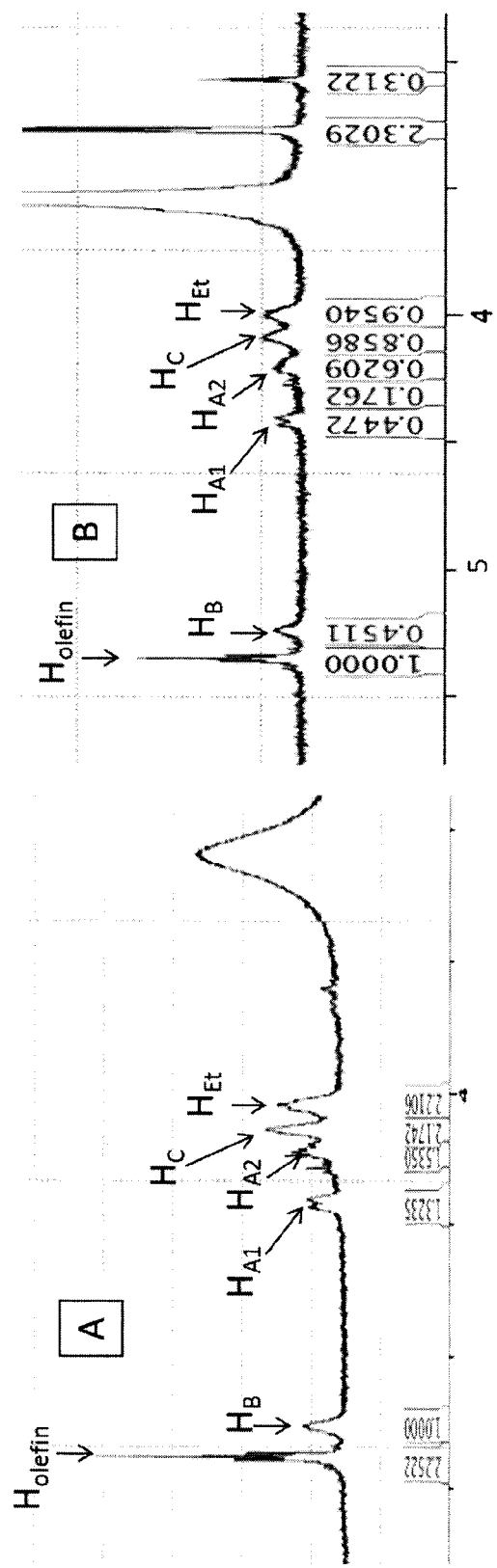
Figure 4:
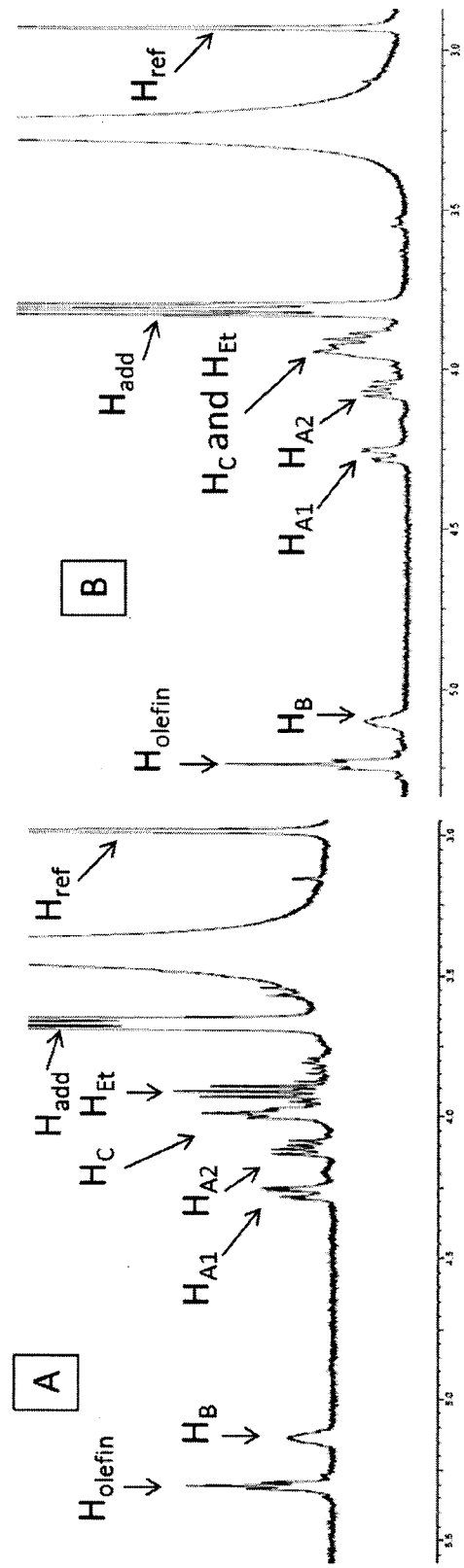
Figure 5:
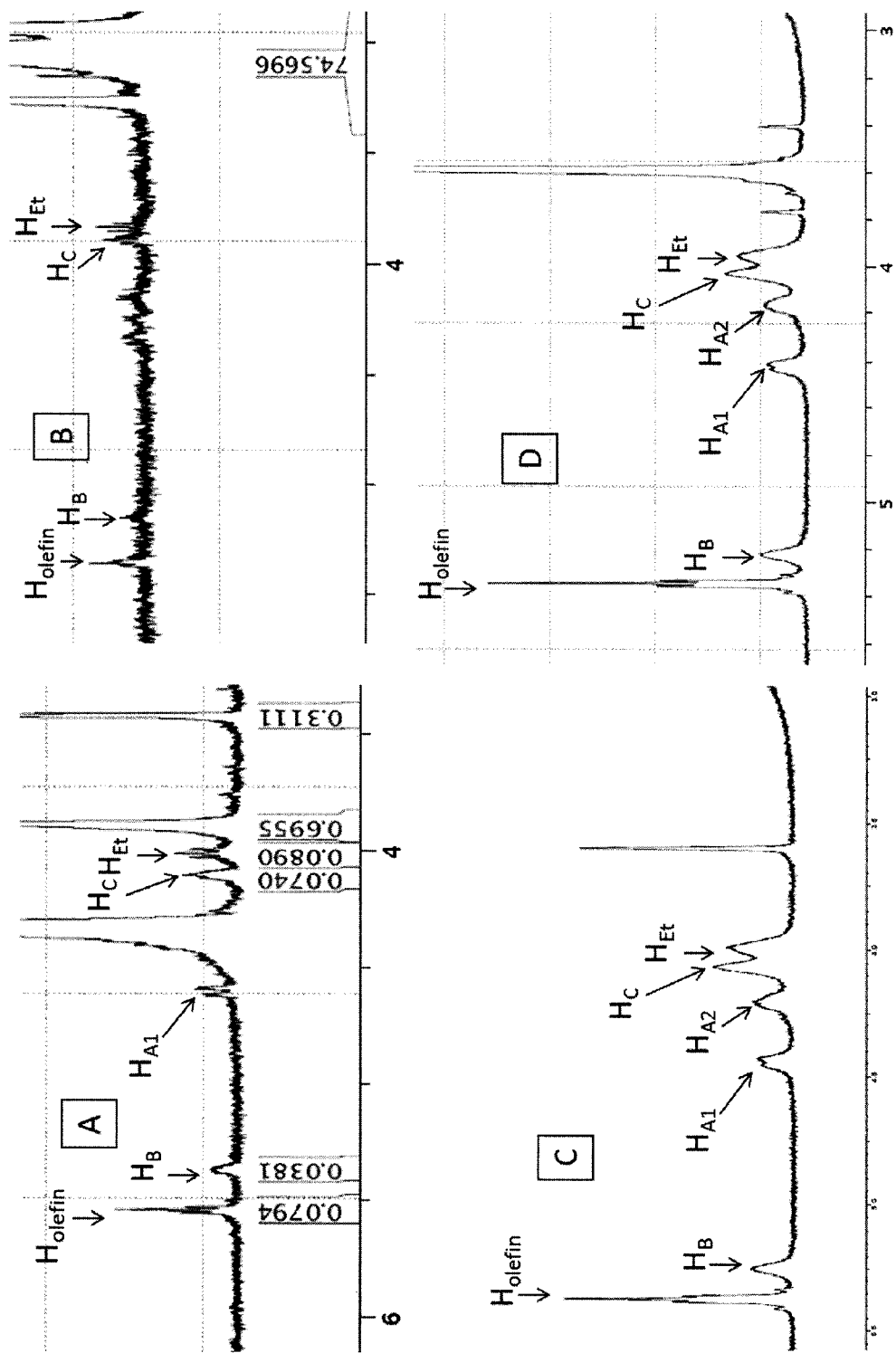
Figure 6:
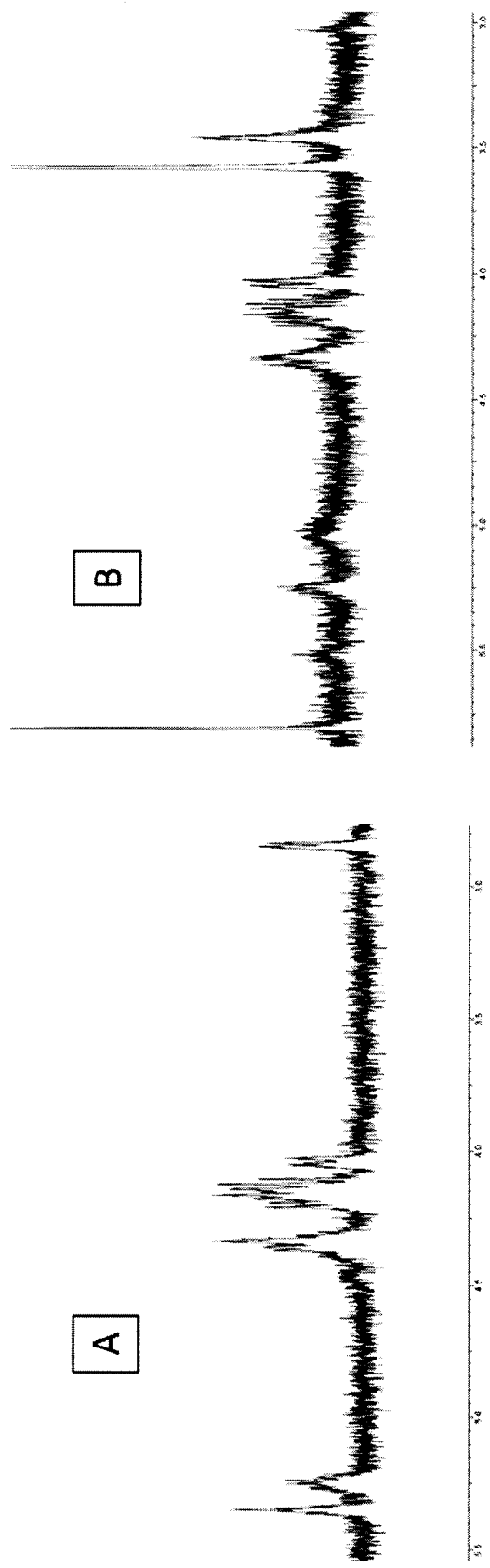
Figure 7:
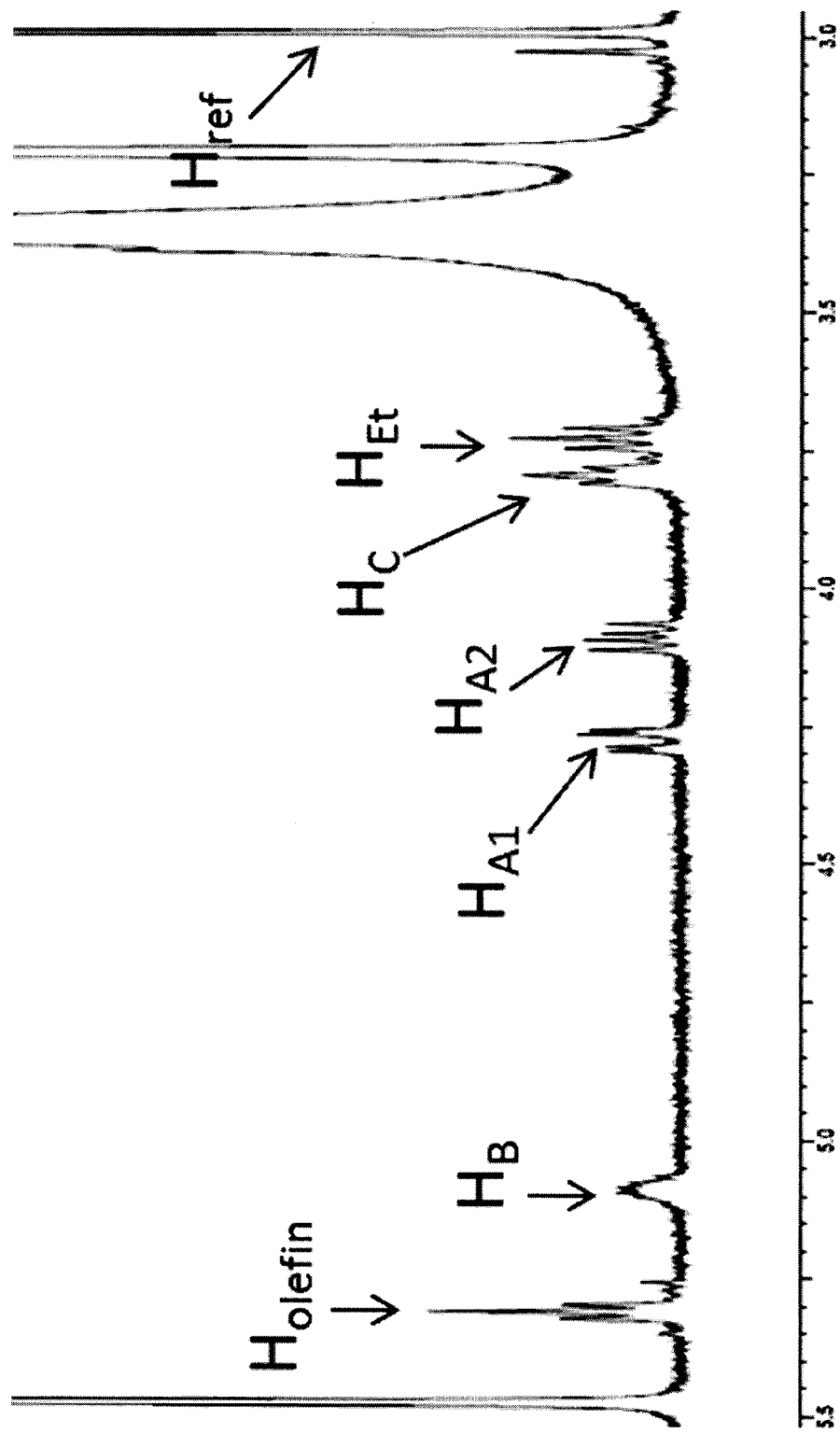
Figure 8:
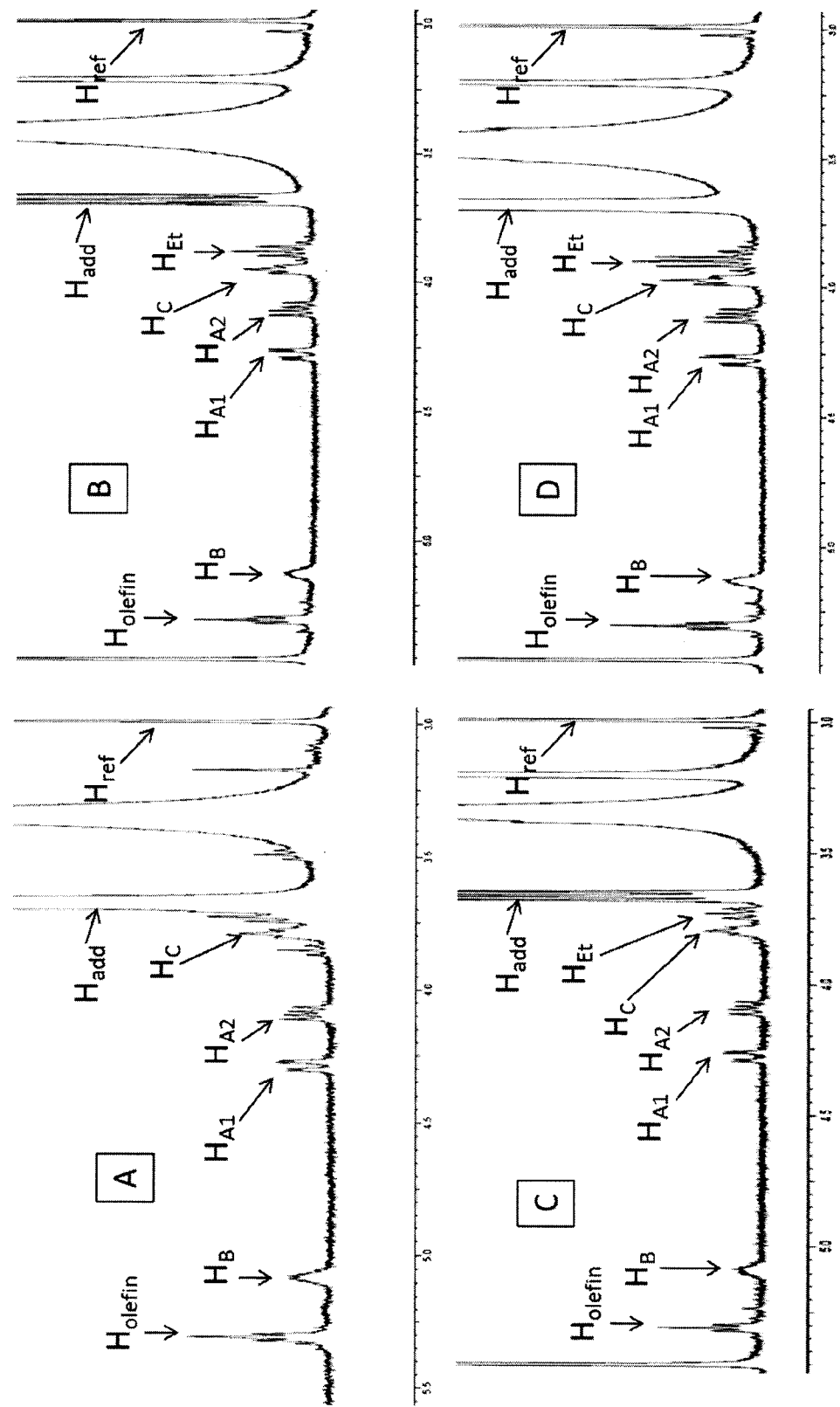
Figure 9:
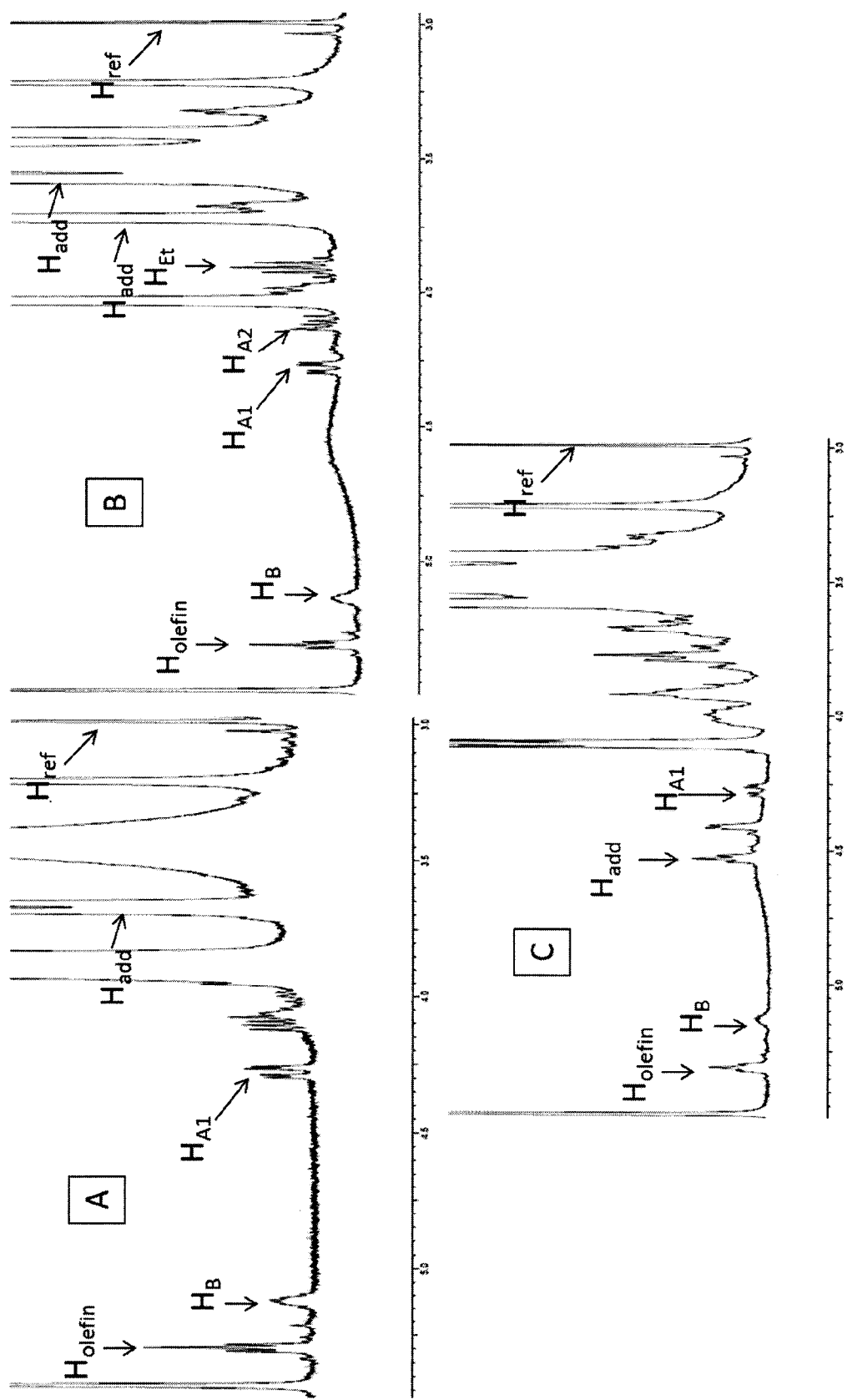
Figure 10:
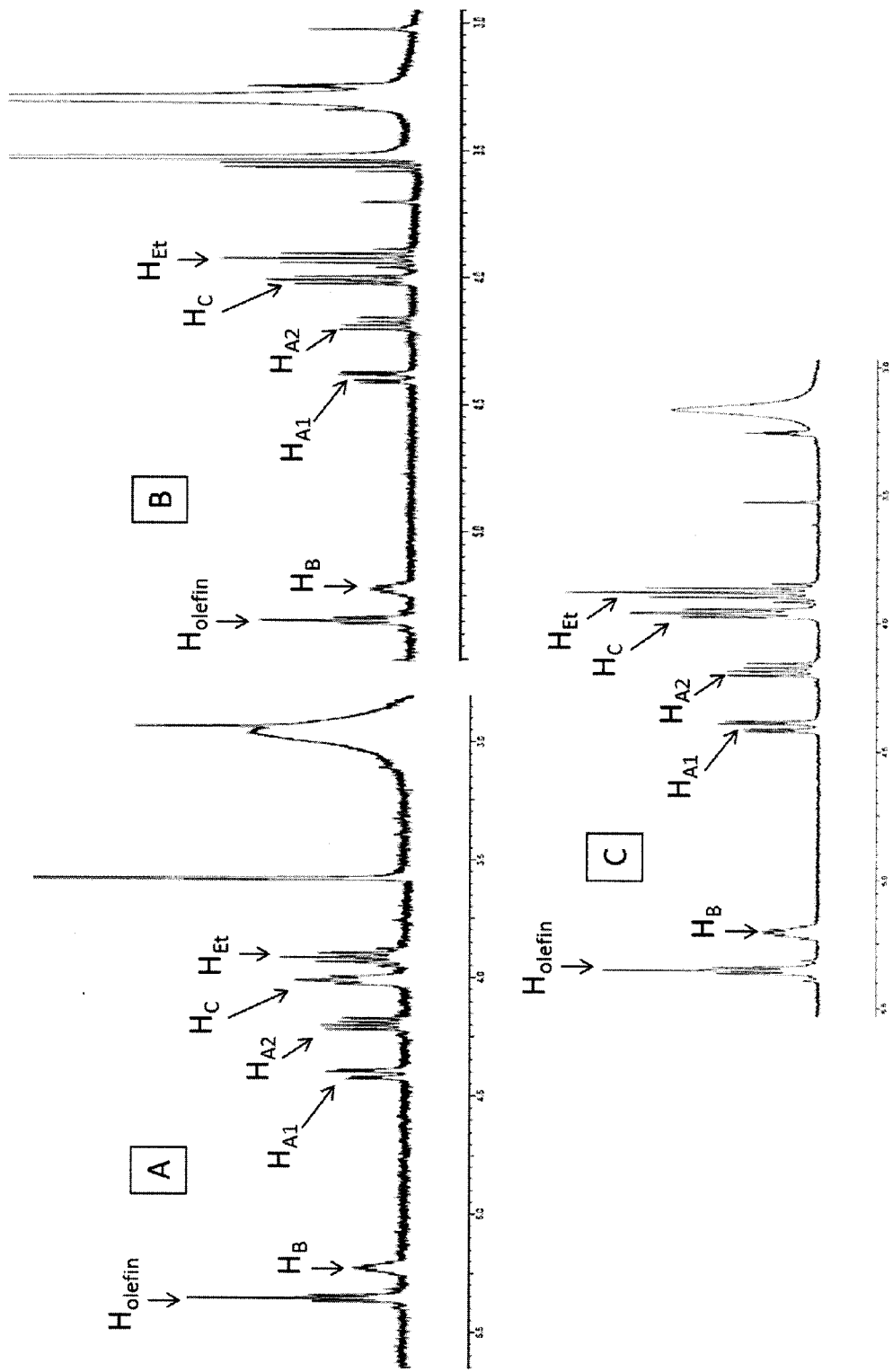
Figure 11:
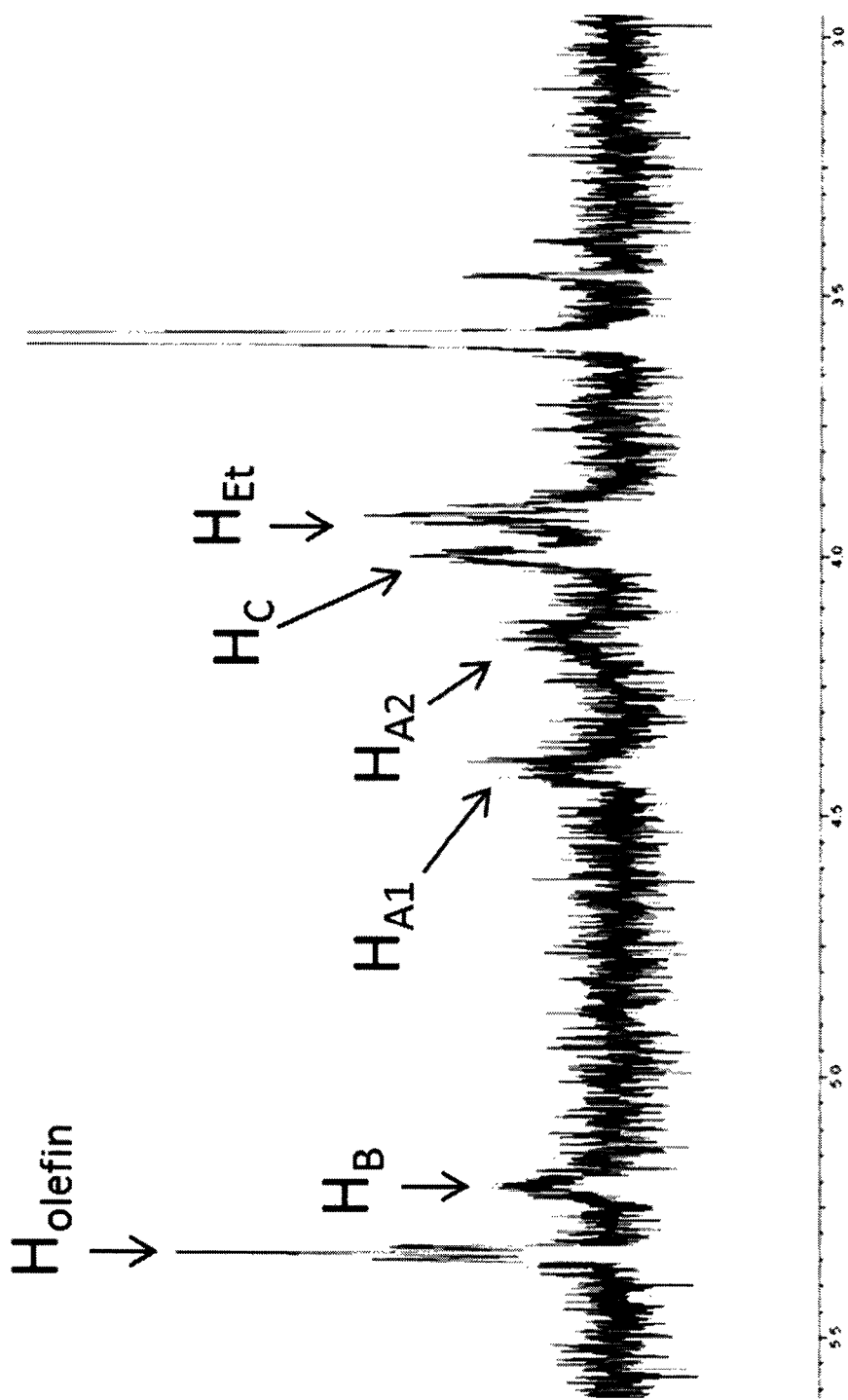

Other aspects, features and advantages of which the invention is capable will be apparent and elucidated from the following description of non-limiting embodiments of the present invention, reference being made to the accompanying figures, in which FIG. 1 shows $^1$H-NMR spectra of the parent protonated form of PEth-16:0/18:1 in: (A) a mixture of CDCl$_3$ (CAS-no: 86549-6) and CD$_3$OD (CAS-no: 811-98-3) (4:1, v:v), and (B) CDCl$_3$ at a concentration of 10 mg/ml, (C) CDCl$_3$ at a concentration of 1 mg/ml;

FIG. 2 shows $^1$H-NMR spectra of the parent protonated form of PEth-16:0/18:1 in: (A) DMSO-d6 (CAS-no: 2206-27-1) with traces of CDCl$_3$ at a concentration of about 3 mg/ml prepared by removal by distillation in vacuo of more than 95% of the CDCl$_3$ from a solution of the parent protonated form of PEth-16:0/18:1 in a mixture of DMSO-d6 and CDCl$_3$ (1:2, v:v), according to one embodiment, (B) DMSO-d6 at a concentration of about 2 mg/ml, and (C) a mixture of DMSO-d6 and CD$_3$OD (4:1, v:v) at a concentration of about 2 mg/ml;

FIG. 3 shows $^1$H-NMR spectra of the parent protonated form of PEth-16:0/18:1 in: (A) acetone-d6 (CAS-no: 666-52-4) at a concentration of about 3 mg/ml, and (B) a mixture of acetone-d6 and CD$_3$OD (4:1, v:v) at a concentration of about 2 mg/ml;

FIG. 4 shows $^1$H-NMR spectra of the parent protonated form of PEth-16:0/18:1 in: (A) a solution of SDS (CAS-no: 151-21-3) (16 mg/ml) in DMSO-d6 with traces of CDCl$_3$ prepared by removal by distillation in vacuo of more than 95% of the CDCl$_3$ from a solution of the parent protonated form of PEth-16:0/18:1 and SDS in a mixture of DMSO-d6 and CDCl$_3$ (1:2, v:v), according to one embodiment, and (B) a solution of SDS (5 mg/ml) in a mixture of DMSO-d6 and CDCl$_3$ (1:2, v:v);

FIG. 5 shows $^1$H-NMR spectra of the parent protonated form of PEth-16:0/18:1 in: (A) a mixture of DMF-d7 (CAS-no: 4472-41-7) and CD$_3$OD (4:1, v:v), (B) a mixture of MeCN-d3 (CAS-no: 2206-26-0) and CD$_3$OD (3:1, v:v), (C) a mixture of acetone-d6 and THF-d8 (CAS-no: 1693-74-9) (1:1, v:v), and (D) THF-d8 at a concentration of about 4 mg/ml;

FIG. 6 shows $^1$H-NMR spectra of different salt form of PEth-16:0/18:1: (A) the ammonium salt form in CDCl$_3$ at a concentration of about 1 mg/ml, and (B) the trimethylammonium salt form in CDCl$_3$ at a concentration of about 1 mg/ml;

FIG. 7 shows the $^1$H-NMR spectrum of a solution of the trimethylammonium salt form of PEth-16:0/18:1 in DMSO-d6 (about 3 mg/ml) obtained by shaking an excess of the trimethylammonium salt form of PEth-16:0/18:1 in DMSO-d6 at 38° C. for 15 min. followed by cooling to 22° C. and decantation, according to one embodiment;

FIG. 8 shows $^1$H-NMR spectra of different salt forms of PEth-16:0/18:1: (A) the ammonium salt form in a solution of SDS (34 mg/ml) in DMSO-d6, (B) the trimethylammonium salt form in a solution of SDS (6 mg/ml) in DMSO-d6 with traces of CH$_2$Cl$_2$ prepared by removal by distillation in vacuo of more than 95% of the CH$_2$Cl$_2$ from a solution of the trimethylammonium salt form of PEth-16:0/18:1 and SDS in a mixture of DMSO-d6 and CH$_2$Cl$_2$ (1:4, v:v), according to one embodiment; (C) the trimethylammonium salt form in a solution of SDS (6 mg/ml) in DMSO-d6 obtained by shaking an excess of the trimethylammonium salt form of PEth-16:0/18:1 with SDS in DMSO-d6 at 38° C. for 15 min. followed by cooling to 22° C. and decantation, according to one embodiment, and (D) the trimethylammonium salt form in a solution of SDS (29 mg/ml) in DMSO-d6 with traces of CH$_2$Cl$_2$ prepared by removal by distillation in vacuo of more than 95% of the CH$_2$Cl$_2$ from a solution of the trimethylammonium salt form of PEth-16:0/18:1 and SDS in a mixture of DMSO-d6 and CH$_2$Cl$_2$ (1:4, v:v), according to one embodiment;

FIG. 9 shows $^1$H-NMR spectra of solutions of the trimethylammonium salt form of PEth-16:0/18:1 in DMSO-d6 with traces of CH$_2$Cl$_2$ in the presence of various amphiphilic additives obtained by removal by distillation in vacuo of more than 95% of the CH$_2$Cl$_2$ from a solution of the trimethylammonium salt form of PEth-16:0/18:1 and the amphiphilic additive in a mixture of DMSO-d6 and CH$_2$Cl$_2$ (1:4, v:v), according to different embodiments: (A) the amphiphilic additive is Na-AOT (CAS-no: 577-11-7) with a concentration of 80 mg/ml, (B) the amphiphilic additive is Triton-X 100 (CAS-no: 9002-93-1) with a concentration of 46 mg/ml, and (C) the amphiphilic additive is Tween 20 (CAS-no: 9005-64-5) with a concentration of 42 mg/ml;

FIG. 10 shows $^1$H-NMR spectra of different salt forms of PEth-16:0/18:1: (A) the trimethylammonium salt form in acetone-d6, (B) the trimethylammonium salt form in a mixture of acetone-d6 and CD$_3$OD (5:1, v:v), and (C) the ammonium salt form in a mixture of acetone-d6 and CD$_3$OD (32:1, v:v); and FIG. 11 shows the $^1$H-NMR spectrum of a solution of the trimethylammonium salt form of PEth-16:0/18:1 in THF-d8 at a concentration of about 1 mg/ml.

DETAILED DESCRIPTION

Definitions

The term "addition salt" or "salt" is intended to mean salts formed by the reaction with a base or by exchange with another cation, in which a negatively charged form of the parent compound is bond to a positively charged form of the base or the cation. The term "addition salt" or "salt" also comprises hydrates and solvent addition forms, such as hydrates and alcoholates, as well as complexes, such as complexes with amines in their neutral or protonated positively charged form.

As used herein, "alkyl" used alone or as a suffix or prefix, is intended to include both branched and straight chain saturated aliphatic hydrocarbon groups having from 1 to 25 carbon atoms or if a specified number of carbon atoms is provided then that specific number is intended. For example "C1-6 alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "N(C0 alkyl)2" is equivalent to "NH2" (amino).

Examples of alkyl include, but are not limited to, methyl, ethyl, n-propyl, propyl, n-butyl, i-butyl, sec-butyl, t-butyl, pentyl, and hexyl.

As used herein, "straight alkyl" used alone or as a suffix or prefix, is intended to include straight chain saturated aliphatic hydrocarbon groups having from 1 to 25 carbon atoms or if a specified number of carbon atoms is provided then that specific number is intended. For example "C1-6 straight alkyl" denotes alkyl having 1, 2, 3, 4, 5 or 6 carbon atoms.

Examples of straight alkyl include, but are not limited to, methyl, ethyl, n-propyl, n-butyl, n-pentyl, n-hexyl, n-heptyl and n-octyl.

As used herein, "alkenyl" used alone or as a suffix or prefix, is intended to include both branched and straight chain olefinic hydrocarbon groups having from 2 to 25 carbon atoms and at least one double bond, or if specified numbers of carbon atoms and double bonds are provided then that specific number is intended. For example "C17-19:1-4 alkenyl" denotes alkenyl having 17, 18 or 19 carbon atoms and 1, 2, 3 or 4 double bonds.

As used herein, "straight alkenyl" used alone or as a suffix or prefix, is intended to include straight chain olefinic hydrocarbon groups having from 2 to 25 carbon atoms and at least one double bond, wherein the double bonds are independently of cis-configuration (Z-configuration) or trans-configuration (E-configuration) and a plurality thereof separated from each other by one carbon atom in between, or if specified numbers of carbon atoms and double bonds are provided then that specific number is intended. For example "C17-19:1-4 straight alkenyl" denotes straight chain alkenyl having 17, 18 or 19 carbon atoms and 1, 2, 3 or 4 double bonds that each independently may be of E- or Z-configuration.

As used herein, "straight Z-alkenyl" used alone or as a suffix or prefix, is intended to include straight chain olefinic hydrocarbon groups having from 2 to 25 carbon atoms and at least one double bond, wherein all double bonds are of cis-configuration (Z-configuration) and a plurality thereof separated from each other by one carbon atom in between, or if specified numbers of carbon atoms and double bonds are provided then that specific number is intended. For example "C17-19:1-4 straight Z-alkenyl" denotes straight chain alkenyl having 17, 18 or 19 carbon atoms and 1, 2, 3 or 4 Z-double bonds.

As used herein, the term "aryl" or "aromatic carbocycle" refers to a ring structure, comprising at least one aromatic ring, made up of from 5 to 14 carbon atoms. Ring structures containing 5, 6, 7 and 8 carbon atoms would be single-ring aromatic groups, for example phenyl. Ring structures containing 8, 9, 10, 11, 12, 13, or 14 carbon atoms would be polycyclic, for example naphthyl. The aromatic ring may be substituted at one or more ring positions. The term "aryl" or "aromatic carbocycle" also includes polycyclic ring systems having two or more cyclic rings in which two or more carbons are common to two adjoining rings (the rings are "fused rings") wherein at least one of the rings is aromatic.

As used herein, "heteroaryl", "hetaryl" or "heterocycle" refers to an aromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen. Heteroaryl, hetaryl or heterocycle groups include monocyclic and bicyclic (e.g., having 2 fused rings) systems. The aromatic ring of the heteroaryl, hetaryl or heterocycle group may be substituted at one or more ring positions.

Examples of heteroaryl or hetaryl groups include without limitation, pyridyl (i.e., pyridinyl), pyrimidinyl, pyrazinyl, pyridazinyl, triazinyl, furyl (i.e. furanyl), quinolyl, tetrahydroquinolyl, isoquinolyl, tetrahydroisoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, benzimidazolyl, indolinyl, and the like.

As used herein, the term "substitutable" refers to an atom to which a hydrogen may be covalently attached, and to which another substituent may be present instead of the hydrogen. A non-limiting example of substitutable atoms include the carbon-atoms of an ethyl group.

As used herein, the term "isotopically enriched" refers to a compound or group in which an isotope of one or several of the composing atoms are present in an amount which is significantly higher than the corresponding naturally occurring amount. Non-limiting examples of isotopically enriched compounds and groups include, for example, $CDCl_3$, dimethylsulfoxide-d6 and $—CDHCH_3$, in which one or several of the substitutable atoms carry the $^2H$-isotope of hydrogen instead of the more common naturally occurring $^1H$-isotope.

EMBODIMENTS OF THE INVENTION

Embodiments of the present invention will be described in more detail below with reference to the accompanying figures in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

Embodiments of the present invention will now be described below with reference to FIGS. 1 to 11.

The composition of the invention essentially comprises a phosphatidylalkanol and a polar water miscible deuterated solvent, typically a deuterated aprotic polar solvent. It was surprisingly discovered that NMR-signals, in particular but not limited to $^1H$-NMR-signals, are generally more well suited for QNMR than corresponding compositions of the prior-art based on lipophilic solvents, such as e.g. $CDCl_3$, as the main constituent. Signals of particular interest, i.e. preferable signals, of phosphatidylalkanols for $^1H$-QNMR, are those that are relatively insensitive to expected contaminants, i.e. which are separated from the signals of the contaminants, which may be formed upon decomposition of the phosphatidylalkanol. Such signals include, but are not limited to:

olefinic signals (herein referred to as "$H_{olefin}$") and allylic signals of unsaturated fatty acid side chains of the phosphatidylalkanol, which are generally well separated from e.g. contaminants resulting from light and oxygen induced allylic oxidation thereof.

Signals originating from hydrogens bound to the glycerol skeleton (herein referred to as "$H_{A1}$", "$H_{A2}$", "$H_B$" and "$H_C$"), of which at least one generally are well separated from contaminants resulting from hydrolytic removal of one or both of the fatty acid side chains or the phosphate or phosphate carried alkanol group.

Signals originating from the hydrogens bound to the alkanol group, in particular those adjacent to the P—O-moiety (herein referred to as "$H_{Et}$"), which are generally well separated from alkanol contaminants resulting from hydrolytic removal of the phosphate or phosphate carried alkanol group.

The same reasoning is valid for other NMR detectable nuclei, such as for example $^{31}P$ and $^{13}C$. The deuterium of the present composition may, for example, advantageously be used for locking the NMR-spectrometer when set up for recording $^1H$, $^{31}P$ and $^{13}C$. Advantages of the present composition include, for example, separation and isolation of at least three of the signals "$H_{olefin}$", "$H_{A1}$", "$H_{A2}$", "$H_B$" and "$H_C$", to a degree whereby integration suitable for QNMR quantification may be performed. In addition, the line shape and fine splitting resolution of at least one of these signals are generally improved in comparison to comparable compositions of the prior-art, which leads to improved QNMR quantification (for example, compare FIG. 1C with 2B; or 1B or 1C with 4A).

According to one embodiment, the composition may comprise a compound of formula I

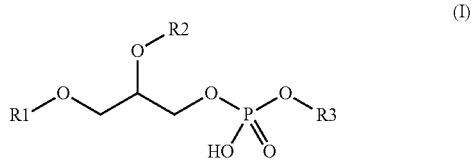

(I)

or any salt, diastereomer, enantiomer, racemic mixture, scalemic mixture or isotopically enriched form thereof and a deuterated aprotic polar solvent. R1 may be selected from the group consisting of —C(=O)—C2-25 straight alkyl, —C(=O)—C2-25:1-6 straight alkenyl and —C(=O)-A-Q. R2 may be selected from the group consisting of —C(=O)—C2-25 straight alkyl, —C(=O)—C2-25:1-6 straight alkenyl and —C(=O)-A-Q. R3 may be —C1-6 alkyl, such as e.g. methyl or ethyl. A may a linker group comprising 2 to 20 carbon atoms, such as e.g. a straight alkylene group comprising 4 to 8 carbon atoms, such as 4 carbon atoms. Q may be a spectrophotometrically or fluorometrically detectable moiety comprising at least one aromatic carbocycle or heterocycle such as e.g. a further substituted or unsubstituted phenyl group. The sum of the compound of formula I and any salt form, diastereomer, enantiomer, racemic mixture, scalemic mixture and isotopically enriched form thereof may exceed 0.05 µmol/g, such as being in the range of 0.5 µmol/g to 10 µmol/g, of said composition. Such a range is optimal with regard to simultaneous facile $^1$H-QNMR and minimized risk for precipitation of the compound of formula I. The deuterated aprotic polar solvent may be miscible with water in any proportion at a temperature such as 20 to 25° C. It may comprise less than 5% residual $^1$H-isotopes such as less than 1, 0.5 or 0.1% residual $^1$H-isotopes, e.g. to enable facile $^1$H-QNMR measurements.

According to one embodiment, R3 may be ethyl and R1 and R2 may represent the esterified form of endogenous carboxylic acids independently selected from the group consisting of saturated fatty acids, ω-3-unsaturated fatty acids, ω-6-unsaturated fatty acids, ω-7-unsaturated fatty acids and ω-9-unsaturated fatty acids.

According to one embodiment, the compound of formula I may represent endogenous PEth-homologues, such as those produced in the human upon exposure to ethanol as well known in the art.

According to one embodiment, the compound of formula I may be isotopically enriched with deuterium or any other suitable isotope as well known in the art. Such an enriched compound may advantageously be used as a reference material in e.g. MS or MS/MS analytical applications. Non-limiting examples of isotopically enriched compounds of formula I include compounds in which the alkanol group, e.g. an ethanol group, is fully deuterated and compounds which comprise at plurality of $^{13}$C isotopes.

According to one embodiment, the deuterated solvent may be an aprotic polar solvent. Non limiting examples of such solvents include acetone-d6, acetonitrile-d3, dimethylsulfoxide-d6, N,N-dimethylformamide-d7 (DMF-d7), N-methyl-2-pyrrolidone-d9, tetrahydrofuran-d8, pyridine-d5, 1,4-dioxane-d8 and diglyme-d14. Additional suitable deuterated aprotic polar solvents are well known in the art and may be selected by the skilled person on basis of the disclosed information herein.

According to one embodiment, the deuterated solvent, e.g. a deuterated aprotic polar solvent, may be a mixture of deuterated polar aprotic solvents.

According to one embodiment, the deuterated solvent, preferably a deuterated aprotic polar solvent, may have a boiling point of at least 80° C., such as at least 100° C. to 150° C., preferable at least 150° C., at atmospheric pressure.

According to one embodiment, the deuterated solvent, preferably a deuterated aprotic polar solvent, may be a readily available and relatively inexpensive solvent such as e.g. dimethylsulfoxide-d6 (DMSO-d6), DMF-d7 or acetone-d6.

According to one embodiment, the present composition may further comprise an amphiphilic additive. Such an amphiphilic additive has a main purpose to aid the dissolution of the compound of formula I in a polar organic or aqueous matrix. Non-limiting examples of amphiphilic additives include detergents selected from the group consisting of anionic-, cationic-, non-ionic- and zwitterionic detergents. Suitable amphiphilic additives selected from these groups, or other suitable amphiphilic additives, may be selected by the skilled person on the basis of mainly the following properties:

Ability to aid dissolution of a lipophilic compound in a polar environment without gel-formation or formation of, from an NMR-perspective, unsuitable formation of micelles.

Minimal disturbing signals in the corresponding NMR-spectrum.

Minimal disturbing behavior in MS and/or MS/MS applications.

The present composition may comprise an amphiphilic additive in an amount exceeding 1 mg/g of the composition, such as 5 to 80 mg/ml of the composition. Non-limiting examples of suitable amphiphilic additives include SDS, Na-AOT, Triton-X 100, Tween 20. Additional suitable amphiphilic additives include analogs and homologues of the before mentioned amphiphilic additives, as depicted in the scheme herein, wherein the sum of w, x, y and z, of which each represents an integer number, may be in the range of 15 to 25, the integer number n may be in the range of 5 to 15, R4 may be C8-25 alkyl, R5 may be C8-25 alkyl and M+ may be an alkali metal cation or ammonium.

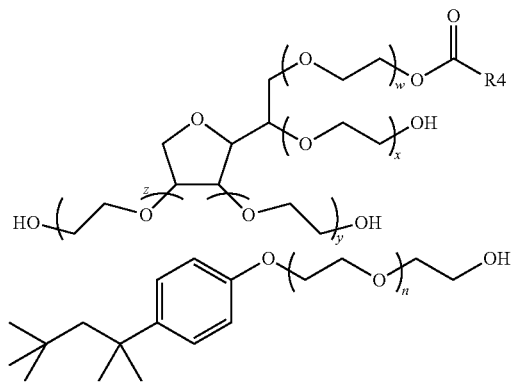

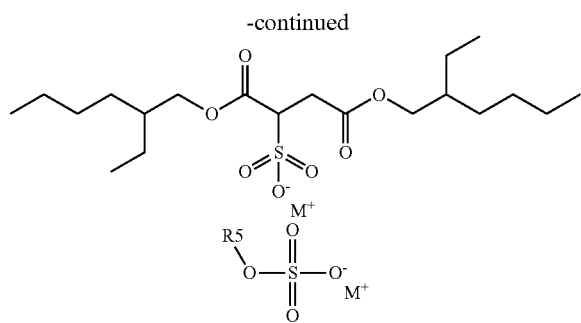

According to one embodiment, the present composition may comprise SDS, or a corresponding analog or homologue as mentioned herein, as an amphiphilic additive, in a range of concentrations selected from 5 to 60, such as 5 to 51 or preferably 25 to 35 mg/ml of the composition. Such a range is optimal with regard to a balance of ability to run $^1$H-QNMR and solubility of the compound of formula I.

According to one embodiment, the present composition may comprise Na-AOT, or a corresponding analog or homologue as mentioned herein, as an amphiphilic additive, in a range of concentrations selected from 5 to 100, such as 19 to 80 or preferably 25 to 50 mg/ml of the composition. Such a range is optimal with regard to a balance of ability to run $^1$H-QNMR and solubility of the compound of formula I.

According to one embodiment, the present composition may comprise Triton-X 100, or a corresponding analog or homologue as mentioned herein, as an amphiphilic additive, in a range of concentrations selected from 5 to 80, such as 8 to 46 or preferably 20 to 40 mg/ml of the composition. Such a range is optimal with regard to a balance of ability to run $^1$H-QNMR and solubility of the compound of formula I.

According to one embodiment, the present composition may comprise Tween 20, or a corresponding analog or homologue as mentioned herein, as an amphiphilic additive, in a range of concentrations selected from 5 to 80, such as 5 to 42 or preferably 20 to 40 mg/ml of the composition. Such a range is optimal with regard to a balance of ability to run $^1$H-QNMR and solubility of the compound of formula I.

According to one embodiment, the present composition may further comprise an internal reference, for the purpose of serving as a quantitative QNMR reference. The internal reference may be present in an amount to allow detection by NMR in period of time which is essentially equal to or less than the period of time needed for detection by NMR of the compound of formula I. The internal reference may further bring forth at least one NMR signal pertaining to an investigated nucleus, which NMR-signal is suitable for integration and which is essentially separated from all NMR-signals of the compound of formula I pertaining to the same investigated nucleus, upon the generation of an NMR-spectrum of the composition. The selection of a suitable internal reference is readily done by the skilled person, who may chose a compound which preferably is commercially available and validated for QNMR applications, which gives a signal suitable for integration in a free region of the NMR-spectra and which signal is not far separated from at least one of signals of interest of the compound of formula I.

According to one embodiment, the present composition may further comprise a strong solvent. Such strong solvent is generally lipophilic and may change the shift of one or several of the NMR-signals of interest into a more suitable region for integration, as well as increase the resolution and fine-splitting of the same (for example, compare FIG. 2A with FIG. 2B or FIG. 8B with FIG. 8C). Non-limiting examples of suitable strong solvents include $CH_2Cl_2$, $CD_2Cl_2$, $CHCl_3$ and $CDCl_3$. Additional strong solvents may be selected by the skilled person on basis of lipophilicity and minimal disturbance of NMR-spectra, and for the purpose of preparability of such a composition, also on the basis of boiling point. The concentration of the strong solvent in the composition may be fine-tuned in order to accomplish an optimal effect. A suitable concentration range may be 0.1 to 10, such as 0.7 to 3.5 or preferably 0.5 to 5 mg/ml of the composition.

According to one embodiment, the present composition may further comprise a polar modifier. Such a polar modifier is generally a polar protic solvent and may change the shift of one or several of the NMR-signals of interest into a more suitable region for integration, as well as increase the resolution and fine-splitting of the same (for example, compare FIG. 2C with FIG. 1A or 2B, or 10B with 10A). Non-limiting examples of suitable strong solvents include short aliphatic alcohols, such as methanol, preferably in a deuterated form. The concentration of the polar modifier in the composition may be fine-tuned in order to accomplish an optimal effect. A suitable concentration range may be 1 to 50, such as 3 to 25 or preferably 10 to 20 vol-% of the composition.

According to one embodiment, the present composition may further comprise a protective additive. Such a protective additive may protect the compound of formula I from decomposition, such as from air and/or light mediated decomposition and/or hydrolytic decomposition. Non-limiting examples of protective additives include antioxidants such as e.g. BHT or sesamol, preservatives, pH adjusting agents, colorants and drying agents.

According to one embodiment, there is provided a salt of a compound of formula I

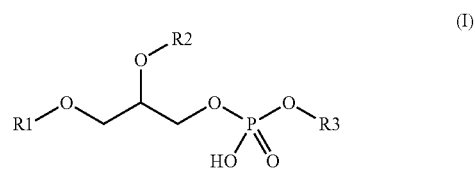

(I)

or any diastereomer, enantiomer, racemic mixture, scalemic mixture or isotopically enriched form thereof. The salt form may be selected from the group consisting of ammonium salts, e.g. the ammonium salt, alkylammonium salts, such as e.g. the methylammonium- or ethylammonium salt, dialkylammonium salts in which the alkyl groups are independently selected alkyl groups, such as e.g. the dimethyl-, diisopropyl- or diethylammonium salt, and trialkylammonium salts in which the alkyl groups are independently selected alkyl groups, such as e.g. the trimethyl-, diisopropylmethyl- or triethyl ammonium salt. The salt may also be a quarternary tetra-alkyl ammonium salt. R1 may be selected from the group consisting of —C(=O))—C2-25 straight alkyl, —C(=O)—C2-25:1-6 straight alkenyl and —C(=O)-A-Q. R2 may be selected from the group consisting of —C(=O)—C2-25 straight alkyl, —C(=O)—C2-25:1-6 straight alkenyl and —C(=O)-A-Q. R3 may be —C1-6 alkyl, such as e.g. methyl or ethyl. A may be a linker group comprising 2 to 20 carbon atoms, such as e.g. a straight alkylene group comprising 4 to 8 carbon atoms, such as 4 carbon atoms. Q may be a spectrophotometrically or fluorometrically detectable moiety comprising at least one aromatic carbocycle or heterocycle such as e.g. a further substituted or unsubstituted phenyl group. R1 and R2 may also represent the esterified form of endogenous carboxylic acids independently selected from the group consisting of saturated fatty acids, ω-3-unsaturated fatty acids, ω-6-unsaturated fatty acids, ω-7-unsaturated fatty acids and ω-9-unsaturated fatty acids.

According to one embodiment, the present composition may comprise the salt of a compound of formula I and a deuterated solvent, such as polar and lipohilic solvents exemplified by DMSO-d6 or acetone-d6 or THF-d8 and $CDCl_3$, respectively. It was unexpectedly found that such a salt form gave improved $^1$H-NMR spectra in comparison to compositions of the prior art (for example, compare FIG. 7 with 1B or 2B, 10A with 1B or 4A, 11 with 1A or 5D, and 1C with 6A or 6B).

According to one embodiment, there is provided a method of production of the composition, comprising the steps of: (i) treating the compound of formula I with a deuterated aprotic polar solvent until all or a part of the compound of formula I is dissolved in the deuterated aprotic polar solvent, to obtain a first intermediate composition; and (ii) if the first intermediate composition comprise any heterogeneous matter, optionally remove the heterogenous matter by filtration or decantation.

According to one embodiment, there is provided a method of production of the composition, comprising the steps of (i) treating the compound of formula I with a strong solvent until all or a part of the compound of formula I is dissolved in the strong solvent, to obtain a second intermediate composition; (ii) mixing the second intermediate composition with a deuterated aprotic polar solvent, to obtain a third intermediate composition; (iii) removing more than 95% of the strong solvent, such as until the strong solvent constitute less than 10 mg/ml, from the third intermediate composition by distillation or evaporation, to obtain a fourth intermediate composition; and (iv) if the fourth intermediate composition comprise any heterogeneous matter, optionally remove the heterogenous matter by filtration or decantation, wherein the strong solvent has a boiling point of at least 20° C. less than the boiling point of the deuterated aprotic polar solvent and in which the solubility of the compound of formula I is at least 1 mg/ml, such as more than 5 mg/ml, of the strong solvent a temperature of 25° C.

According to one embodiment, there is provided a method for determination of the concentration of a compound of formula I in the composition by QNMR, such as $^1$H-, $^{31}$P- and $^{13}$C-QNMR, comprising the steps of: (i) collecting at least two NMR signals pertaining to an investigated nucleus of the composition; (ii) collecting the integral of at least one isolated NMR signal brought forth by the compound of formula I and at least one isolated NMR signal brought forth by a determinative component; and (iii) calculating the concentration of the compound of formula I on the basis of the integrals collected in step (ii), wherein the amount of the determinative component or the concentration of the determinative component in the composition may be known; the determinative component may be selected from the group consisting of residual protonated solvent in the deuterated solvent, preferably a deuterated aprotic polar solvent, when the investigated nucleus of the composition is $^1$H, the amphiphilic additive, the internal reference, an external reference and the additive.

According to one embodiment, the present composition may be used for the production of an analytical standard solution. The composition may, for example, be diluted in an aqueous solution, such as e.g. the initial mixture used in gradient LC-MS(/MS), to a desired concentration, whereby such a standard solution is obtained.

Preferred combinations, each representing an embodiment of the invention, of the form of a compound of formula I, the deuterated solvent, the internal reference, the strong solvent, the polar modifier and the amphiphilic additive of the composition of the invention, are listed in the table herein (embodiment #1 to 29).

| Embodiment # | Form of Compound of formula I (H: protonated parent form; NH3: ammonium salt; NMe3: trimethyl-ammonium salt) | Deuterated solvent | Internal reference | Strong solvent | Concentration of strong solvent (mg/ml) | Polar modifier | Concentration of polar modifier (vol-%) | Amphiphilic additive | Concentration of amphiphilic additive (mg/ml) |
|---|---|---|---|---|---|---|---|---|---|
| 1 | H | DMSO-d6 | dimethyl sulfone | none | N.A. | none | N.A. | Triton-X 100 | 20 to 40 |
| 2 | " | " | " | $CH_2Cl_2$, $CD_2Cl_2$, $CHCl_3$ or $CDCl_3$ | 0.5 to 5 | " | " | " | " |
| 3 | " | " | " | " | " | " | " | SDS | 25 to 35 |
| 4 | NMe3 | " | " | " | " | " | " | " | " |
| 5 | " | " | " | " | " | $CD_3OD$ | 10 to 20 | " | " |
| 6 | " | " | " | none | N.A. | " | " | " | " |
| 7 | " | " | " | " | " | " | " | Triton-X 100 | 20 to 40 |
| 8 | " | " | " | " | " | none | N.A. | " | " |
| 9 | " | " | " | " | " | " | " | SDS | 25 to 35 |
| 10 | NH3 | " | " | " | " | " | " | " | " |
| 11 | " | " | " | $CH_2Cl_2$, $CD_2Cl_2$, $CHCl_3$ or $CDCl_3$ | 0.5 to 5 | " | " | " | " |
| 12 | " | " | " | " | " | $CD_3OD$ | 10 to 20 | " | " |
| 13 | " | " | " | none | N.A. | " | " | " | " |
| 14 | " | " | " | " | " | none | N.A. | Triton-X 100 | 20 to 40 |
| 15 | " | acetone-d6 | none or suitable | " | " | " | " | " | " |
| 16 | " | " | " | " | " | $CD_3OD$ | 10 to 20 | " | " |

-continued

| Embodiment # | Form of Compound of formula I (H: protonated parent form; NH3: ammonium salt; NMe3: trimethyl-ammonium salt) | Deuterated solvent | Internal reference | Strong solvent | Concentration of strong solvent (mg/ml) | Polar modifier | Concentration of polar modifier (vol-%) | Amphiphilic additive | Concentration of amphiphilic additive (mg/ml) |
|---|---|---|---|---|---|---|---|---|---|
| 17 | " | " | " | " | " | none | N.A. | SDS | 25 to 35 |
| 18 | " | " | dimethyl sulfone | " | " | CD₃OD | 10 to 20 | " | " |
| 19 | NMe3 | " | " | " | " | " | " | none | N.A. |
| 20 | " | " | " | " | " | " | " | SDS | 25 to 35 |
| 21 | " | " | none or suitable | " | " | none | N.A. | " | " |
| 22 | " | " | " | " | " | " | " | Triton-X 100 | 20 to 40 |
| 23 | H | " | " | " | " | " | " | " | " |
| 24 | " | DMF-d7 | " | " | " | " | " | SDS | 25 to 35 |
| 25 | " | " | " | CH₂Cl₂, CD₂Cl₂, CHCl₃ or CDCl₃ | 0.5 to 5 | " | " | " | " |
| 26 | " | " | " | none | N.A. | CD₃OD | 10 to 20 | " | " |
| 27 | " | " | " | " | " | " | " | none | N.A. |
| 28 | NH3 | " | " | " | " | " | " | SDS | 25 to 35 |
| 29 | NMe3 | " | " | " | " | " | " | " | " |

Reversed positional PEth isomers (RPI-PEth's) have been found to be present as a minor counterpart for various PEth-homologues, e.g. PEth-16:0/18:1 and PEth-16:0/18:2, in various samples, e.g. present PEth-comprising reference samples of the prior-art and human blood samples. The structure of a typical generic RPI-PEth is shown below (structure labelled "RPI-PEth"), wherein "UFA" represents an unsaturated fatty acid residue with at least one C—C-double bond, e.g. —C(=O)—C2-25:1-6 straight alkenyl, and "SFA" represents a saturated fatty acid residue with no double bonds, e.g. —C(=O)—C2-25 straight alkyl.

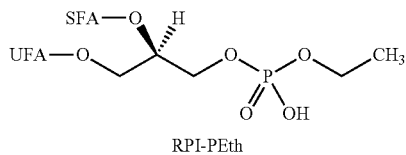

RPI-PEth

Without being bound to any theory, the inventors believe that such RPI-PEths originate from the corresponding RPI-PCs, from which PEth may be synthesized endogenously or biomimetically by employment of PLD. It is previously known that various amounts of RPI-PCs occur for several PCs in different biological systems, like e.g. humans. Similar chromatographic and spectral properties, as well as identical molecular weights, make a RPI-PEth difficult to differentiate analytically from the corresponding PEth. Analogous to the corresponding isomeric pairs among the PCs, it was found that the relative intensities of commonly studied secondary fragments of RPI-PEths in MS/MS-applications are different from the corresponding PEths. Hence, an unknown error in the LC-MS/MS quantification of individual PEth-homologues is introduced when this quantification is based on such second fragment intensities unless the isomeric distribution is accounted for. Herein is disclosed novel RPI-PEths useful as analytical references. These references may, for example, be used in compositions comprising an appropriate amount of the corresponding PEth for more accurate calibration of e.g. LC-MS/MS-instruments to mimic the natural isomeric distribution of PEth/RPI-PEth in the species, e.g. human, of interest.

Endogenous phospholipase activity may result in the formation of lyso-PEth metabolites by cleavage of the carboxylic acid residue at sn-2 of the parent PEth. The structure of a typical generic lyso-PEth is shown below (structure labelled "lyso-PEth"). The corresponding structure in which the SFA- and the UFA-residues have switched places represent a typical lyso-RPI-PEth, as illustrated below. Herein disclosed embodiments, examples and reasoning regarding lyso-PEth is to be understood applicable to the corresponding lyso-RPI-PEth, as readily understood by the skilled person. Lyso-PEth may also be formed by biosynthesis from lyso-PC. Not only may lyso-PEth serve as an ethanol bio-marker per-se, but the relationship between the levels of lyso-PEth and the corresponding PEth may hold additional information relating to a person's drinking behavior. For example, if the PEth and the corresponding lyso-PEth have different half-life in-vivo, the relationship between the corresponding levels enable the skilled person to differ between the following two cases, which may result in similar levels of PEth: a) the person has consumed a relatively large amount of ethanol a relatively long time ago, and b) the person has consumed a relatively small amount of ethanol a relatively short time ago.

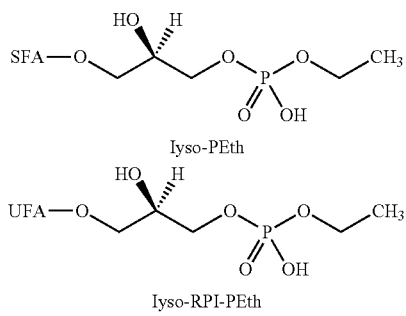

lyso-PEth lyso-RPI-PEth

Herein are disclosed novel lyso-PEths and lyso-RPI-PEths useful as analytical references. These references may, for example, be used as references in the calibration of analytical instruments, e.g. LC-MS/MS-instruments, for quantification of lyso-PEth in a person's blood. Comparison of the levels of lyso-PEth and corresponding PEth may enable the skilled person to differ between cases a) and b) above.

d5-PEths (i.e. penta-deuterated PEths) have a molecular weight that is about 5 units higher than the corresponding non-labeled lipids. This difference enables use of d5-PEth as internal standard in analytical applications based on e.g. LC-MS(/MS) techniques. The structure of a typical generic d5-PEth is shown below (structure labelled "d5-PEth"). The corresponding structure in which the SFA- and the UFA-residues have switched places represent a typical d5-RPI-PEth, as illustrated below. Herein disclosed embodiments, examples and reasoning regarding d5-PEth is to be understood applicable to the corresponding d5-RPI-PEth, as readily understood by the skilled person.

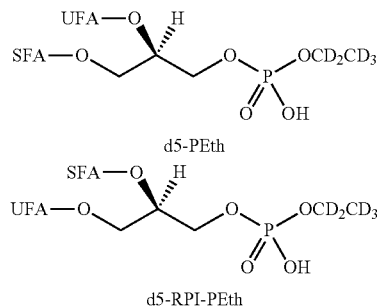

Herein is disclosed novel d5-PEths and/or d5-RPI-PEths useful as analytical references. These references may, for example, be used as references, such as e.g. internal references, in the calibration of or when using analytical instruments, e.g. LC-MS/MS-instruments, for quantification of PEth or RPI-PEth, respectively, in a person's blood.

Compounds of Formula I and II may be prepared from readily available glycerol derivatives carrying a suitable protective group on the hydroxyl group, which eventually becomes attached to the phosphorous atom in the final compound of Formula I or II, according to one embodiment. For example, para-methoxybenzyl (PMB) may be used as such a protective group as illustrated in the exemplary synthetic scheme herein for the synthesis of PEth, d5-PEth, RPI-PEth, lyso-PEth, d5-RPI-PEth, lyso-RPI-PEth and d5-lyso-RPI-PEth, each belonging to the group of compounds represented by compounds of Formula I or II. In the synthetic scheme(s), a SFA is exemplified as palmitoyl and an UFA as oleoyl or linoleoyl, according to one embodiment. These exemplifications are, however, not to be understood as limiting, but rather serving as suitable examples to aid the skilled person in fully understanding the invention. The following reagents and conditions may be used to furnish the indicated yields of the desired products: (i) SFA or UFA (1.05 eq.), N,N'-dicyclohexylcarbodiimide (DCC, 1.05 eq.), 4-dimethylaminopyridine (DMAP, 0.05 eq.), DCM, 0° C. to rt (35 to 45%), (ii) SFA or UFA (1.4 eq.), DCC (1.4 eq.), DMAP (0.1 eq.), dichloromethane (DCM), rt (91 to 99.6%), (iii) 2,3-dichloro-5,6-dicyano-1,4-benzoquinone (DDQ, 1.05 eq.), DCM:H2O (96:4, v:v), rt (29% of 7a, 77% of 6c), (iv) ceric ammonium nitrate (CAN, 10 eq.), acetonitrile: H2O (9:1, v:v), rt (13 to 89% of 7b-d), (v) 9 (for 8, 10b and 10d) or 9-d5 (for 11) (2.0 eq.), tetrazole (2.2 eq), acetonitrile: THF (1:2.6, v:v), rt, then H2O2 (30% aq., 8 eq.), (vi) THF: 25% aq. ammonia (9:1, v:v), rt (25 to 58%, two steps), (vii) ethyl dichlorophosphate (EDCP, 2.5 eq.), triethylamine (5.2 eq.), DCM, 0° C. to rt (16 to 22%), (viii) 3,4-dihydro-2H-pyran (2.0 eq.), pyridinium p-toluenesulfonate (0.2 eq.), DCM, rt (quant.). Minor amounts of 2-acylated and 1,2-diacylated by-products may be formed in step i, but these may easily be separated from the desired 1-acylated monoesters 2, 3 and 4 by chromatography on silica gel. Conditions and reagents (iv) are preferred over (iii) for the synthesis of 7a-d due to a less tendency of acylmigration and thereby formation of undesired 6a-d. Phosporylation employing reagent 9 or 9-d5 is generally preferred over phosphorylation employing EDCP due to higher yields of the desired products. The tetrahydropyranyl (THP) protective group of 13 was simultaneously cleaved of during phosphorylation employing EDCP (conditions vii) in the synthesis of lyso-PEth 14. Lyso-PEths, e.g. 14, and the corresponding d5-lyso-PEths may be prepared from 13, or corresponding derivatives carrying other fatty acid residues but palmitoyl, by phosphorylation employing reagent 9 and 9-d5, respectively, followed by mild acidic deprotection of the thp-group and basic removal of the cyanoethyl-group, as well known in the art. The desired salt forms of compounds of the invention, e.g. 10a-d, 10a', 11 and 14, may be obtained by appropriate choice of eluent system in chromatographic purification on silica gel of the crude materials. In order to obtain the parent protonated form in the case of lyso-PEths, e.g. 14, and d5-lyso-PEths the gradient system toluene: acetone:acetic acid:water (6:4:0:0 to 55:36:7:2) may be used. For retrieval of the ammonium and trimethylammonium salts, like e.g. in the case of 8, 10a-d, 11a,b and 10a', the gradient systems DCM:toluene:abs. ethanol: 25% aq. ammonia (80:9:10:1 to 74:8:17:1) and DCM:toluene:abs. ethanol: 13% trimethylamine in THF (79:9:10:2 to 70:8:20:2) or DCM:toluene:methanol: 28% aq. trimethylamine (87.5:9:3:0.5 to 77:12:10:1), respectively, may be used.

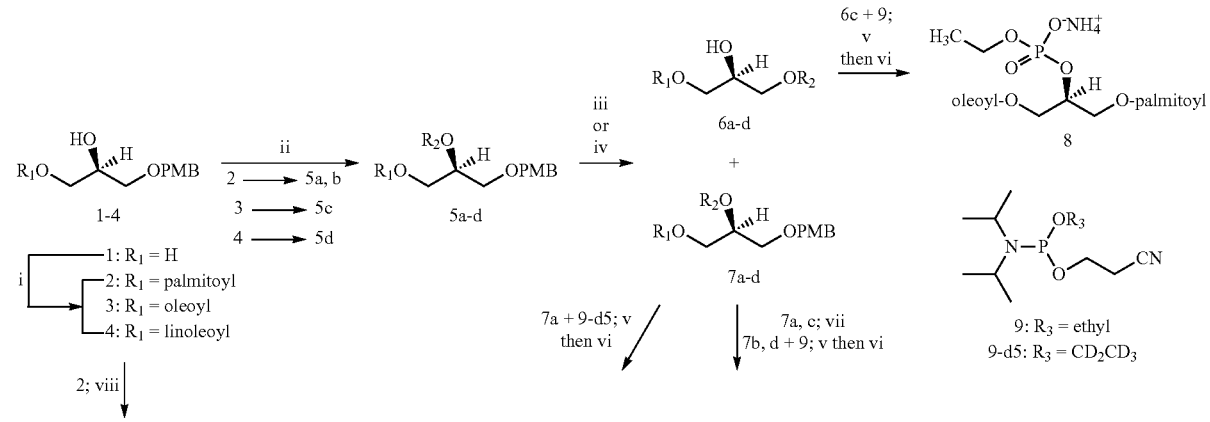

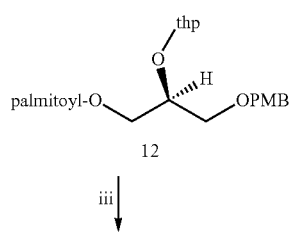
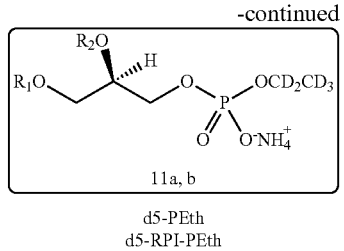
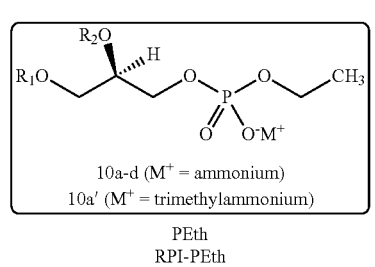

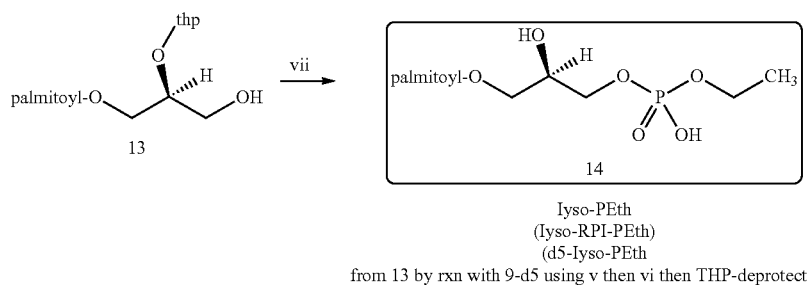

SERIES
a: $R_1$ = palmitoyl; $R_2$ = oleoyl
b: $R_1$ = palmitoyl; $R_2$ = tinoleoyl
c: $R_1$ = oleoyl; $R_2$ = palmitoyl
d: $R_1$ = tinoleoyl; $R_2$ = palmitoyl Compounds of Formula I, II and III may be prepared from readily available glycerol derivatives by initial or early introduction of the phosphorous containing moiety in a protected form, according to one embodiment and as exemplified below. For example, 1,2-isopropylidene-sn-glycerol may initially be phosphorylated (conditions v) by employment of 9 or 9-d5. The 1,2-isopropylidene protective group of the obtained simultaneously cyanoethyl-protected product 15 may be removed by mild acidic treatment (conditions ix), such as e.g. by treatment at ambient temperature or reflux in 5 to 30 vol-% aqueous acetic acid, such as 10 vol-%, or 0.5 to 2 M aq. HCl at ambient temperature, with or without the presence of an organic co-solvent, such as e.g. 10 to 70 vol-% THF or dioxane, or by any method well known in the art that does not severely affect the cyanoethyl-group, to yield diol 16 (representatives of the group of compounds of Formula III). Regio-selective introduction of a carboxylic acid residue, e.g. a SFA or an UFA, onto the sn-1 hydroxyl may then be carried out under e.g. conditions i, to yield intermediate 17. In order to obtain compounds selected from the group consisting of lyso-PEth, d5-lyso-PEth, lyso-RPI-PEth and d5-lyso-RPI-PEth, the cyanoethyl-group of a suitably substituted 17 may be removed by treatment under suitable basic conditions, such as according to conditions vi, or by treatment under any other suitable conditions used for removal of a cyanoethyl-group as well known in the art. In order to obtain compounds selected from the group consisting of PEth, d5-PEth, RPI-PEth and d5-RPI-PEth, introduction of a carboxylic acid residue, e.g. a SFA or an UFA, onto the sn-2 hydroxyl may then be carried out to obtain a suitably substituted intermediate 18, before removal of the cyanoethyl-group as described.

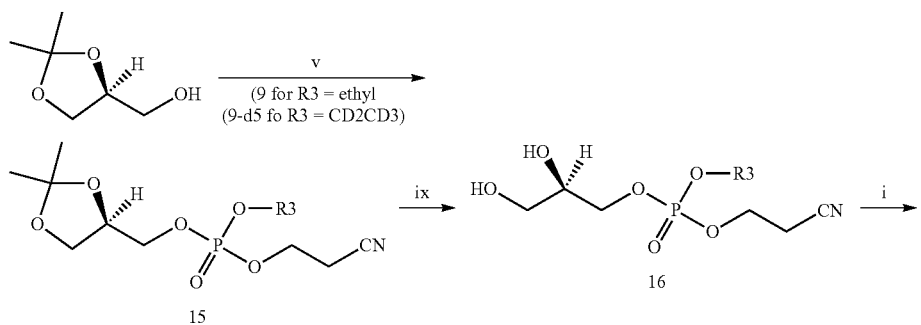

-continued

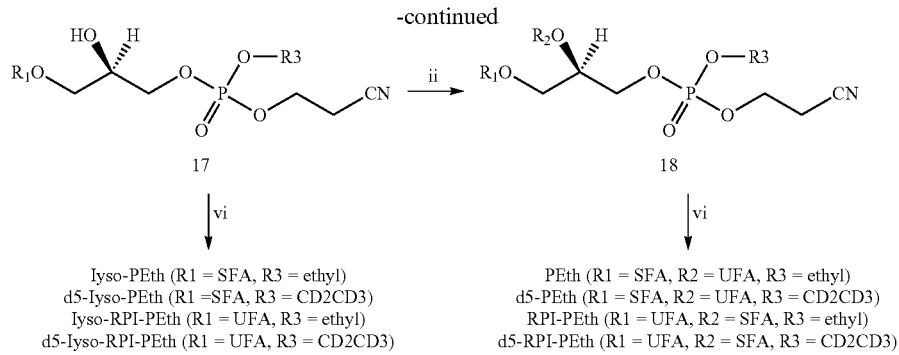

lyso-PEth (R1 = SFA, R3 = ethyl)
d5-lyso-PEth (R1 = SFA, R3 = CD2CD3)
lyso-RPI-PEth (R1 = UFA, R3 = ethyl)
d5-lyso-RPI-PEth (R1 = UFA, R3 = CD2CD3)

PEth (R1 = SFA, R2 = UFA, R3 = ethyl)
d5-PEth (R1 = SFA, R2 = UFA, R3 = CD2CD3)
RPI-PEth (R1 = UFA, R2 = SFA, R3 = ethyl)
d5-RPI-PEth (R1 = UFA, R2 = SFA, R3 = CD2CD3)

Alternative protective groups, as well known in the art, may be used instead of the 1,2-isopropylidene protective group of the simultaneously cyanoethyl-protected compound 15. The skilled person will understand that such a protective group will need to be removed under conditions which will not significantly affect the rest of compound 15, e.g. the cyanoethyl-group. Non-limiting examples of such protective groups include silyl based groups, e.g. TBDMS, and benzyl. The former may be removed with mild F-containing reagents, and the latter by hydrogenation in the presence of a transition metal catalyst, e.g. palladium on carbon. Additional examples of suitable protective groups include acyl-groups, e.g. acetyl och acetyl substituted with electron withdrawing groups, e.g. trichloroacetyl.

PEths and d5-PEths of the invention carrying an oxidative sensitive UFA comprising more than one double bond, e.g. linoleoyl, at the sn-2 position, may be synthesized from intermediates carrying an SFA at the sn-1 position, a THP at the sn-2 position and an oxidatively cleavable benzyl type protective group at the sn-3 position, like e.g. compound 12. The sn-3 protective group may first be cleaved off under oxidative conditions, like e.g. conditions iii or iv. The resulting free hydroxyl may then be phosphorylated by employment of 9 or 9-d5, followed by removal of the thp-group
under mild acidic conditions well known in the art to reveal a free sn-2 hydroxyl. The oxidative sensitive UFA may then be introduced at the sn-2 hydroxyl before final removal of the cyanoethyl group, both steps e.g. in accordance with methods described herein. By the described way of carrying out the oxidative cleavage of the sn-3 protective group prior to the introduction of the sensitive UFA, undesired side products resulting from oxidation mediated reactions of the UFA are advantageously avoided.

EXAMPLES OF COMPOUNDS

One embodiment of the invention relates to a process for preparing salts of a compound according to formula I by chromatography of the corresponding compound of formula I in its protonated parent form or in any salt form by use of an eluent comprising a volatile free base of the corresponding salt to be obtained. Other embodiments of the invention are related to specific salt forms of compounds of formula I, such as e.g. ammonium-, alkylammonium-, dialkylammonium- and trialkylammonium salt forms thereof, as exemplified herein by non-limiting specific examples.

Compound Example 1

The Trimethylammonium Salt of PEth-16:0/18:1, Example of a Compound of the Invention

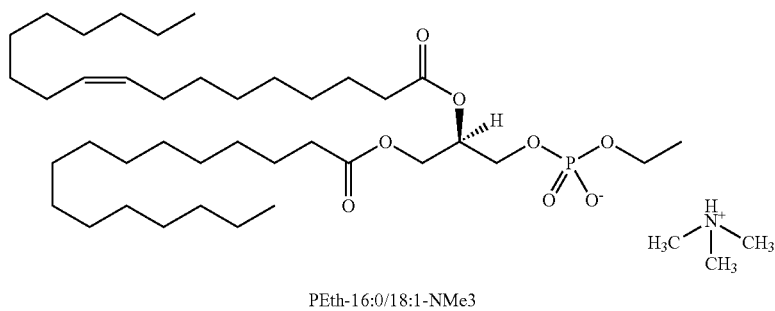

PEth-16:0/18:1-NMe3

A cylindrically shaped silica gel column, with a height of 85 mm and with a diameter of 50 mm, was set up by allowing a slurry of silica gel in a first mixture of $CH_2Cl_2$, toluene, abs. ethanol and 13 wt-% trimethylamine in THF (79:9:10:2, v:v:v:v) to settle by gravity therein. 400 mg of the protonated parent form of PEth-16:0/18:1 (PEth-16:0/18:1-H) was then applied to the top of the column. Elution was thereafter performed employing a gradient starting with the first mixture and ending with a second mixture consisting of $CH_2Cl_2$, toluene, abs. ethanol and 13 wt-% trimethylamine in THF (70:8:20:2, v:v:v:v). Collected fractions (50 ml) were monitored by TLC using the second mixture for elution and a mixture of 4-anisaldehyde (1 ml), conc. $H_2SO_4$ (1 ml) and acetic acid (0.5 ml) in abs. ethanol (30 ml) for developing the spots. Fractions comprising the title compound, as judged by use of PEth-16:0/18:1-H as TLC reference, were pooled and concentrated in vacuo to yield 362 mg of PEth-16:0/18:1-NMe3 as an off-white solid. Examples of $^1$H-NMR spectra in various matrixes of the obtained PEth-16:0/18:1-NMe3 are shown in FIGS. 6B, 7, 8B, 8C, 8D, 9A, 9B, 9C, 10A, 10B and 11.

Compound Example 2

The Ammonium Salt of PEth-16:0/18:1

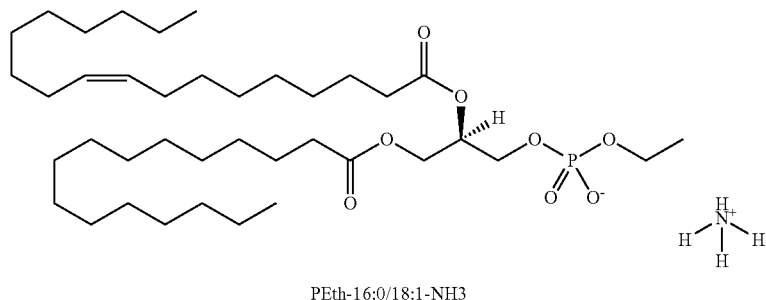

PEth-16:0/18:1-NH3

A cylindrically shaped silica gel column, with a height of 50 mm and with a diameter of 50 mm, was set up by allowing a slurry of silica gel in a first mixture of $CH_2Cl_2$, toluene, abs. ethanol and 25 wt-% aqueous ammonia (80:9:10:1, v:v:v:v) to settle by gravity therein. 70 mg of PEth-16:0/18:1-NMe3 was then applied to the top of the column. Elution was thereafter performed employing a gradient starting with the first mixture and ending with a second mixture consisting of $CH_2Cl_2$, toluene, abs. ethanol and 25 wt-% aqueous ammonia (74:8:17:1, v:v:v:v). Collected fractions (50 ml) were monitored by TLC using the second mixture for elution and a mixture of 4-anisaldehyde (1 ml), conc. $H_2SO_4$ (1 ml) and acetic acid (0.5 ml) in abs. ethanol (30 ml) for developing the spots. Fractions comprising the title compound, as judged by use of PEth-16:0/18:1-NMe3 as TLC reference, were pooled and concentrated in vacuo to yield 38 mg of PEth-16:0/18:1-NH3 as an off-white waxy solid. Examples of $^1$H-NMR spectra in various matrixes of the obtained PEth-16:0/18:1-NH3 are shown in FIGS. 6A, 8A and 10C.

Specific embodiments of the invention relates to compounds of Formula II, to compounds of Formula III and to methods for the production of compounds of Formula II and/or III, as exemplified herein by non-limiting specific examples.

Compound Example 3

1-Palmitoyl-3-(4-methoxybenzyl)-sn-glycerol (2), example of synthetic intermediate To a cool (0° C.) mixture of 3-(4-methoxybenzyl)-sn-glycerol 1 (4.245 g, 20.0 mmol), palmitic acid (5.385 g, 21.0 mmol) and DMAP (122 mg, 1.0 mmol) in dry DCM (100 ml) was added while stirring over 14 h, by employment of a syringe pump, a solution of DCC in dry DCM (0.874 M, 24.0 ml, 21.0 mmol). The reaction mixture was then allowed to attain ambient temperature over 12 h and the formed precipitate was removed by filtration. The filtrate was washed with DCM (3×50 ml) before concentration of the combined DCM portions and purification of the obtained crude material by chromatography on silica gel (gradient from n-heptane to n-heptane:ethyl acetate:i-PrOH 67.5:30:2.5) to yield 4.096 g (45% yield) of the title compound as a colorless waxy solid. A slower eluting fraction (2.49 g, 28% yield) comprising a 9:1-mixture of the title compound and the byproduct 2-palmitoyl-3-(4-methoxybenzyl)-sn-glycerol, as evident by the presence of a separate pentet at 5.04 ppm and a separate multiplet at 3.59 to 3.68 ppm ($^1$H-NMR, 400 MHz, chloroform-d), was also obtained.

Compound Example 4

1-Oleoyl-3-(4-methoxybenzyl)-sn-glycerol (3), example of synthetic intermediate

The title compound was prepared according to the procedure for the preparation of 2 from 3-(4-methoxybenzyl)-sn-glycerol 1 (5.00 g, 23.56 mmol), oleic acid (6.32 g, 22.38 mmol), DMAP (280 mg, 2.36 mmol) and DCC in dry DCM (1.031 M, 24.0 ml, 24.74 mmol) to yield 5.08 g (48% yield) of the title compound as a colorless waxy solid.

Compound Example 5

1-Palmitoyl-2-oleoyl-3-(4-methoxybenzyl)-sn-glycerol (5a), example of synthetic intermediate Compound 2 (2.398 g, 5.32 mmol), oleic acid (1.65 g, 5.85 mmol), DCC (1.208 g, 5.85 mmol) and DMAP (65 mg, 0.53 mmol) was stirred in DCM (100 ml) at ambient temperature for 16 h. Another portion of each of oleic acid (451 mg, 1.60 mmol) and DCC (329 mg, 1.60 mmol) was then added, followed by stirring for another 16 h before removal of the formed precipitate by filtration. The filtrate was the washed with DCM (3×50 ml) before concentration of the combined DCM portions and purification of the obtained crude material by chromatography on silica gel (gradient from n-heptane to n-heptane:ethyl acetate 9:1) to yield 3.465 g (91% yield) of the title compound as a colorless syrup that slowly crystallized.

Compound Example 6

1-Oleoyl-2-palmitoyl-3-(4-methoxybenzyl)-sn-glycerol (5c), example of synthetic intermediate The title compound was prepared according to the procedure for the preparation of 5a from 3 (2.89 g, 6.22 mmol)

and palmitic acid (1.75 g, 6.84 mmol) to yield 4.42 g (99.3% yield) of the title compound as a colorless syrup that slowly crystallized.

Compound Example 7

1-Oleoyl-3-palmitoyl-sn-glycerol (6c), example of synthetic intermediate

To a stirred mixture of 5c (3.29 g, 4.60 mmol) and water (3.0 ml) in DCM (75 ml) was added 2,3-dichloro-5,6-dicyano-1,4-benzoquinone (1.09 g, 4.83 mmol) in one portion. After stirring at ambient temperature for 7 h, the reaction mixture was filtered through a short plug of Celite® and concentrated. The obtained residue was purified by chromatography on silica gel (gradient from DCM to DCM:i-PrOH 97.5:2.5). Besides slightly more slowly eluting fractions, which contained various amounts of the title compound and 1-oleoyl-2-palmitoyl-sn-glycerol 7c, 2.107 g (77% yield) of the title compound was obtained in a pure form as a white solid.

Compound Example 8

1-Palmitoyl-2-linoleoyl-sn-glycerol (7b), example of synthetic intermediate

To a rapidly stirred mixture of 1-palmitoyl-2-linoleoyl-3-(4-methoxybenzyl)-sn-glycerol 5b (668 mg, 0.936 mmol) and water (1.0 ml) in acetonitrile (9.0 ml) was added CAN (5.13 g, 9.36 mmol). Stirring was continued at ambient temperature for 3 h before pouring onto brine (50 ml) and extraction with DCM (50+3×20 ml). The combined organics were dried over sodium sulphate and concentrated to furnish the crude material. Purification by chromatography on silica gel (n-heptane:ethyl acetate 9:1) gave 115 mg (21% yield) of the title compound as a colorless oil.

Compound Example 9

1-Linoleoyl-2-palmitoyl-sn-glycerol (7d), example of synthetic intermediate

The title compound was prepared according to the procedure for the preparation of 7b from 1-linoleoyl-2-palmitoyl-3-(4-methoxybenzyl)-sn-glycerol 5d (1.409 g, 1.976 mmol) to yield 150 mg (13% yield) of the title compound as a colorless oil.

Compound Example 10

2-Cyanoethoxy-(ethoxy)-(N,N-diisopropylamino)phosphine (9), example of synthetic intermediate To a cool (0° C.) and stirred solution of 2-cyanoethyl-N,N-diisopropylchlorophosphoramidite (892 µL, 4.0 mmol) in dry DCM (20 ml) was added, in consecutive order, triethylamine (586 µL, 4.2 mmol) and abs. ethanol (245 µL, 4.2 mmol). The reaction mixture was then allowed to attain ambient temperature and stirred for another 50 min. before concentration in vacuo. The residue was treated with diethyl ether (10+2×5 ml) followed by filtration to remove solids through a syringe filter. The filtered solution was concentrated by a slow stream of nitrogen to furnish 911 mg (92% yield) of the crude title compound as a yellowish oil. This oil was dissolved in dry THF (15.2 ml) to provide a solution (60 mg/ml) which was used directly as reagent in further reactions described herein.

Compound Example 11

2-Cyanoethoxy-(1,1,2,2,2-petadeuteroethoxy)-(N,N-diisopropylamino)phosphine (9-d5), example of a compound of the invention The title compound was prepared according to the procedure used for the preparation of 9, with the only exception that dry deuterated ethanol (ethanol-d5) was used instead of abs. ethanol, to furnish 945 mg (94% yield) the title compound as a yellowish oil. $^1$H-NMR (400 MHz, chloroform-d) δ ppm 1.19 (dd, J=6.7, 4.2 Hz, 12H), 2.65 (t, J=6.6 Hz, 2H), 3.54-3.68 (m, 2H), 3.76-3.92 (m, 2H).

Compound Example 12

1-Oleoyl-2-ethoxyhydroxyphosphinyl-3-palmitoyl-sn-glycerol ammonium salt (8)

To 6c (297 mg, 0.50 mmol) was added a solution of 9 in dry THF (60 mg/ml, 4.1 ml, 1.0 mmol) while stirring at ambient temperature. A solution of tetrazole in acetonitrile (0.45 M, 2.55 ml, 1.15 mmol) was then added and stirring was continued for another 2 h before addition of aqueous hydrogen peroxide (35 wt %, 387 µL, 4.5 mmol). The reaction mixture was then stirred for another 30 min. before partitioning between water (50 ml) and DCM (25 ml). The aqueous phase was extracted with DCM (3×20 ml), the combined organics washed with saturated aqueous sodium hydrogen carbonate and dried over sodium sulphate before concentration in vacuo, to provide 422 mg of the crude cyanoethyl protected intermediate as colorless oil. This oil was then stirred in a mixture of THF (4.5 ml) and aqueous ammonia (25 wt %, 0.5 ml) at ambient temperature for 24 h before concentration in vacuo and purification of the obtained residue by chromatography on silica gel (DCM:toluene:abs. ethanol:aqueous ammonia 25 wt %, gradient from 80:9:10:1 to 74:8:17:1). The title compound (Rf=0.4 using DCM:toluene:methanol:aqueous ammonia 25 wt %, 75:12:12:1, as analytical eluent) was obtained as a white solid (208 mg, 58% yield).

Compound Example 13

1-Linoleoyl-2-palmitoyl-3-ethoxyhydroxyphosphinyl-sn-glycerol ammonium salt (10d), example of a compound of the invention The title compound was prepared according to the procedure used for the preparation of 8 from 7d (75.5 mg, 0.1273 mmol), to furnish 40.4 mg (39.5% yield) the title compound as a white solid. $^1$H-NMR (400 MHz, acetone-d6: methanol-d4 97:3) δ ppm 0.85-0.92 (m, 6H), 1.21 (t, J=7.1 Hz, 3H), 1.24-1.42 (m, 38H), 1.61 (sex, J=7.0 Hz, 4H), 2.05-2.12 (m, 4H), 2.32 (q, J=7.6 Hz, 4H), 2.80 (t, J=6.4 Hz, 2H), 3.88 (q, J=7.2 Hz, 2H), 3.96 (t, J=5.8 Hz, 2H), 4.18 (dd, J=12.0, 6.8 Hz, 1H), 4.41 (dd, J=12.0, 3.4 Hz, 1H), 5.17-5.24 (m, 1H), 5.28-5.43 (m, 4H) 13C NMR (acetone-d6: methanol-d4 97:3) δ ppm 14.45, 16.93, 17.00, 23.43, 25.75, 25.78, 27.92, 29.97, 30.17, 30.19, 30.23, 30.40, 30.54, 30.59, 32.33, 32.75, 34.61, 34.82, 48.42, 48.63, 48.84, 49.05, 49.27, 61.17, 61.83, 63.31, 64.18, 64.23, 71.44, 71.53, 130.61, 130.69, 173.37, 173.60; MS (LCMS-ESI−) m/z 699.5 (M-H).

Compound Example 14

1-Palmitoyl-2-oleoyl-3-ethoxyhydroxyphosphinyl-sn-glycerol trimethylammonium salt (10a'), example of a compound of the invention To a cool (0° C.) solution of ethyl dichlorophosphate (401 mg, 2.46 mmol) in dry DCM was added triethylamine (0.512 g, 5.12 mmol) while stirring. A solution of 1-palmitoyl-2-oleoyl-sn-glycerol 7a (586 mg, 0.984 mmol) in dry DCM (2.0 ml) was then added over a period of 5 min. The reaction mixture was then allowed to attain ambient temperature and stirred for 1 h before quench by pouring onto saturated aqueous sodium hydrogen carbonate (10 ml). Extraction with DCM (10+3×5 ml) and concentration in vacuo then followed to provide a crude product that was purified by chromatography on silica gel (DCM:toluene:abs. ethanol:13 wt %, trimethylamine in THF, gradient from 79:9:10:2 to 70:8:20:2). The title compound (Rf=0.3 using DCM:toluene:methanol:aqueous ammonia 25 wt %, 75:12:12:1, as analytical eluent) was obtained as a white solid (134 mg, 18% yield). $^1$H-NMR (400 MHz, acetone-d6: methanol-d4 97:3) δ ppm 0.85-0.92 (m, 6H), 1.23 (t, J=7.1 Hz, 3H), 1.24-1.42 (m, 44H), 1.61 (sex, J=7.0 Hz, 4H), 2.05-2.08 (m, 4H), 2.32 (q, J=7.6 Hz, 4H), 3.92 (q, J=7.2 Hz, 2H), 4.00 (dd, J=6.5, 5.4 Hz, 2H), 4.18 (dd, J=12.0, 6.8 Hz, 1H), 4.40 (dd, J=12.0, 3.4 Hz, 1H), 5.18-5.26 (m, 1H), 5.30-5.40 (m, 2H), 5.77 (s, 9H).

Compound Example 15

1-Palmitoyl-2-(2-tetrahydropyranyl)-3-(4-methoxybenzyl)-sn-glycerol (12), example of synthetic intermediate A mixture of 2 (0.901 g, 2.0 mmol), 3,4-dihydro-2H-pyran (0.336 g, 4.0 mmol) and pyridinium p-toluenesulfonate (0.100 g, 0.40 mmol) was stirred in dry DCM (10 ml) at ambient temperature for 14 h. Volatile matter was then removed by a stream of nitrogen and the obtained residue was purified by chromatography on silica gel (gradient from n-heptane to n-heptane:ethyl acetate:i-PrOH 80:18:2) to yield 1.05 g (98% yield) the title compound as a colorless oil.

Compound Example 16

1-Palmitoyl-2-(2-tetrahydropyranyl)-sn-glycerol (13), example of synthetic intermediate The title compound was prepared according to the procedure used for the preparation of 6c from 12 (1.03 g, 1.926 mmol), with the only exception that a gradient from n-heptane to n-heptane:ethyl acetate:i-PrOH 80:18:2 was used in the purification on silica gel, to furnish 0.511 g (62% yield) the title compound as a white solid.

Compound Example 17

1-Palmitoyl-3-ethoxyhydroxyphosphinyl-sn-glycerol (14), example of a compound of the invention The title compound was prepared according to the procedure used for the preparation of 10a' from 13 (266 mg, 0.642 mmol), with the only exception that a gradient from toluene:acetone 6:4 to toluene:acetone:acetic acid:water 55:36:7:2 was used in the purification on silica gel, to furnish 63 mg (22% yield) the title compound as a glass. 1H-NMR (400 MHz, chloroform-d) δ ppm 0.88 (t, J=6.8 Hz, 3H), 1.23-1.34 (m, 27H), 1.59 (br. s, 2H), 2.25-2.38 (m, 2H), 3.45-3.68 (m, 7H); MS (LCMS-ESI−) m/z 437.3 (M-H).

EXAMPLES OF COMPOSITIONS

Composition Example 1

Preparation from Solution by Concentration in Vacuo

A 10-ml flask with an arrow-shaped bottom was charged with the compound of formula I PEth-16:0/18:1-H (7.5 mg), the internal reference dimethyl sulfone (1.3 mg), the amphiphilic additive (0 mg), followed by addition of the strong solvent $CDCl_3$ (1.5 ml). After shaking the mixture until dissolution, the deuterated solvent DMSO-d6 (0.75 ml) was added and the flask was applied to a rotary evaporator operating at 200 rpm in vacuo, at 22° C. over night. The obtained solution was transferred to an NMR-tube by decantation, followed by $^1$H-NMR recording to furnish the spectrum showed in FIG. 2A.

The Composition Examples 1 to 11 were carried out in analogy to Composition Example 1 described herein above, as summarized in the table herein. Estimation of the final concentration of the compound of formula I and the concentration of the residing strong solvent in the deuterated solvent was done by comparison of $^1$H-NMR-integrals thereof with the $^1$H-NMR-integral of the internal reference.

| Composition Example # | Compound of formula I | strong solvent | deuterated solvent | internal reference | amphiphilic additive/final concentration (mg/ml) | $^1$H-NMR spectrum | estimated concentration of residual strong solvent in final solution (mg/ml) | estimated concentration of compound of formula I in final solution (mg/ml) |
|---|---|---|---|---|---|---|---|---|
| 1 | Peth-16:0/18:1-H | $CDCl_3$ | DMSO-d6 | dimethyl sulfone | no additive | FIG. 2A | | 3 |
| 2 | " | " | " | " | SDS/16 | FIG. 4A | | 6 |
| 3 | " | " | " | " | SDS/24 | | | 7 |
| 4 | Peth-16:0/18:1-NMe3 | $CH_2Cl_2$ | " | " | no additive | | 0.7 | 3 |
| 5 | " | " | " | " | SDS/6 | FIG. 8B | | |
| 6 | " | " | " | " | SDS/29 | FIG. 8D | 3.3 | 5 |
| 7 | " | " | " | " | Na-AOT/19 | | 1.3 | 4 |
| 8 | " | " | " | " | Na-AOT/80 | FIG. 9A | 3.1 | 8 |
| 9 | " | " | " | " | Triton-X 100/8 | | 1 | 4 |
| 10 | " | " | " | " | Triton-X 100/46 | FIG. 9B | 1.3 | 8 |
| 11 | " | " | " | " | Tween 20/42 | FIG. 9C | 3.5 | 7 |

Composition Examples 1 to 11 clearly indicate that the presence of an amphiphilic additive increases the solubility of compounds of formula I in the deuterated solvent in comparison to the case when such an additive is absent.

Composition Example 12

Preparation of Composition "AA55" by Shaking

To a 15-ml flask charged with SDS (505.6 mg) was added DMSO-d6 (10 ml), followed by dissolution by shaking. The total weight of the solution (solution A) was 11.7894 g. PEth-16:0/18:1-NMe3 (30 mg) and the antioxidant BHT (2,6-di-tert-butyl-4-methylphenol, CAS-no: 128-37-0, 1.7 mg) was then added to solution A, followed by closing of the flask and gently shaking it for 4 h at ambient temperature (22° C.). The resulting solution was decanted from heterogeneous matter and filtered through a cotton-plug to yield a composition entitled "AA55" of the invention, comprising PEth-16:0/18:1-NMe3, the detergent SDS and the antioxidant BHT in the deuterated solvent DMSO-d6. AA55 was swept with $N_2$ and stored in the dark at ambient temperature. It was found to be stable under these conditions for a prolonged time over several weeks. Five aliquots (in the range of 460.3 to 475.4 mg) were taken from AA55 and individually mixed with five individually prepared solutions in DMSO-d6 of QNMR-verified commercially available dimethyl sulfone (Sigma-Aldrich, #8012968580; 238.5 to 239.1 mg; 0.523 to 0.544 mg/g). $^1$H-QNMR spectra were collected for each of the resulting mixtures. The signals relating to PEth-16:0/18:1-NMe3 at 5.06-5.12 ppm ($H_B$), 4.26-4.31 ppm ($H_{A1}$) and 4.06-4.12 ppm ($H_{A2}$), and the signal relating to dimethyl sulfone at 2.99 ppm, were integrated. The resulting list of integrals was used to calculate the concentration of PEth-16:0/18:1-NMe3 in "AA55", as summarized in the drawing herein.
COMPOSITION "AA55"—Concentration of Constituting Components Composition Example 13

Preparation by Shaking and Heating

A mixture of PEth-16:0/18:1-NMe3 (15 mg), dimethyl sulfone (0.4 mg) and DMSO-d6 (0.75 ml) was shaken at 38° C. for 15 min. The mixture was then allowed to reach ambient temperature (22° C.) and kept at that temperature for 1 h. The solution was then separated from a glassy precipitate by decantation and transferred to an NMR-tube. The concentration of PEth-16:0/18:1-NMe3 in the solution was estimated to be about 3 mg/ml by comparison of $^1$H-NMR integrals in the $^1$H-NMR spectrum (FIG. 7) of signals from PEth-16:0/18:1-NMe3 with the signal of dimethyl sulfone.

As evident by comparison of the final concentration of PEth-16:0/18:1-NMe3 in the resulting composition of Composition Example 12, with the resulting composition of Composition Example 13, heating of the shaken mixture results in a higher final concentration as compared to the case when the shaken mixture is not heated, even in some cases when the non-heated mixture comprise a detergent. It may be assumed that the obtained concentration upon employment of the heat-cool procedure (Composition Example 13) reflects the thermodynamically controlled limit of solubility, while the obtained concentration upon employment of the simple shake procedure (Composition Example 13) is kinetically limited.

Composition Example 14

Preparation by Shaking and Heating

A mixture of PEth-16:0/18:1-NMe3 (15 mg), dimethyl sulfone (0.4 mg), SDS (4.5 mg) and DMSO-d6 (0.75 ml) was shaken at 38° C. for 15 min. The mixture was then allowed to reach ambient temperature (22° C.) and kept at that temperature for 1 h. The solution was then separated

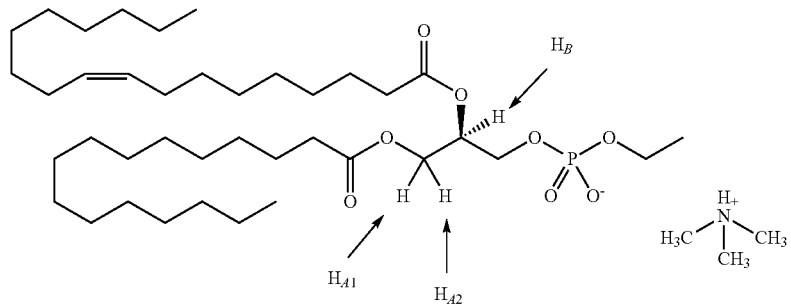

PEth-16:0/18:1-NMe3
$C_{PEth\text{-}16:0/18:1\text{-}NMe3}$ = 1.2 umol/g (0.90 mg/g)

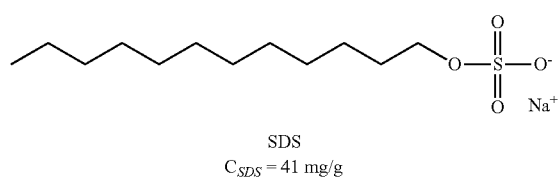

SDS
$C_{SDS}$ = 41 mg/g

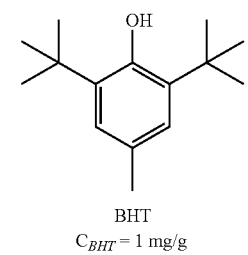

BHT
$C_{BHT}$ = 1 mg/g from a glassy precipitate by decantation and transferred to an NMR-tube. A zoom-in region of the ¹H-NMR spectrum is shown in FIG. 8C.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A salt of a compound of formula I

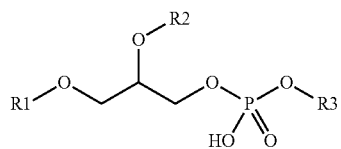

(I)

or any diastereomer, enantiomer, racemic mixture, scalemic mixture or isotopically enriched form thereof, wherein R1 is selected from the group consisting of —C(=O)—C2-25 straight alkyl, —C(=O)—C2-25:1-6 straight alkenyl and —C(=O)-A-Q;

R2 is selected from the group consisting of —C(=O)—C2-25 straight alkyl, —C(=O)—C2-25:1-6 straight alkenyl and —C(=O)-A-Q;

R3 is methyl or ethyl;

A is a linker group comprising 2 to 20 carbon atoms;

Q is a spectrophotometrically or fluorometrically detectable moiety comprising at least one aromatic carbocycle or heterocycle; and said salt is selected from the group consisting of alkylammonium salts, dialkylammonium salts in which the alkyl groups are independently selected alkyl groups, trialkylammonium salts in which the alkyl groups are independently selected alkyl groups, and a quaternary tetra-alkyl ammonium salt.

2. The salt according to claim 1, wherein
R1 and R2 represent an esterified form of endogenous carboxylic acids independently selected from the group consisting of saturated fatty acids, ω-3-unsaturated fatty acids, ω-6-unsaturated fatty acids, ω-7-unsaturated fatty acids and ω-9-unsaturated fatty acids.

3. A salt of the compound of Formula I

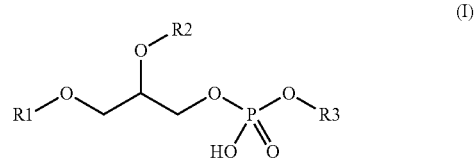

(I)

or any diastereomer, enantiomer, racemic mixture, scalemic mixture or isotopically enriched form thereof, wherein R1 is —C(=O)—C2-25 straight alkyl;

R2 is —C(=O)—C2-25:1-6 straight alkenyl; and

R3 is methyl or ethyl, wherein the salt is selected from the group comprising alkyl ammonium salts, di-alkyl ammonium salts, tri-alkyl ammonium salts, and a quaternary tetra-alkyl ammonium salt.

4. A salt of the compound of Formula I

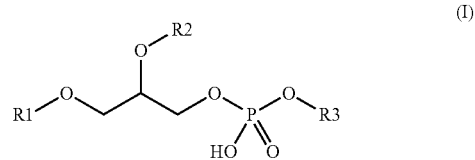

(I)

or any diastereomer, enantiomer, racemic mixture, scalemic mixture or isotopically enriched form thereof, wherein R1 and R2 are esterified endogenous carboxylic acids selected from the group consisting of saturated fatty acids and ω-9-unsaturated fatty acids, R3 is methyl or ethyl, and wherein the salt is selected from the group comprising alkyl ammonium salts, di-alkyl ammonium salts, tri-alkyl ammonium salts, and a quaternary tetra-alkyl ammonium salt.

* * * * *

UNITED STATES PATENT AND TRADEMARK OFFICE
CERTIFICATE OF CORRECTION

PATENT NO. : 9,499,572 B2
APPLICATION NO. : 14/888802
DATED : November 22, 2016
INVENTOR(S) : Wensbo Posaric et al.

Page 1 of 1

It is certified that error appears in the above-identified patent and that said Letters Patent is hereby corrected as shown below:

On the Title Page

Item (72), Line 2, change the incorrect spelling "Karl-Erik Berquist" to the correct spelling of --Karl-Erik Bergquist--.

Signed and Sealed this
Thirteenth Day of February, 2018

Andrei Iancu
*Director of the United States Patent and Trademark Office*